US011702661B2

(12) United States Patent
Blainey et al.

(10) Patent No.: US 11,702,661 B2
(45) Date of Patent: Jul. 18, 2023

(54) CONSTRUCTS FOR CONTINUOUS MONITORING OF LIVE CELLS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Jacob Borrajo, Cambridge, MA (US); Mohamad Najia, Cambridge, MA (US); Atray Dixit, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 793 days.

(21) Appl. No.: 16/335,512

(22) PCT Filed: Sep. 21, 2017

(86) PCT No.: PCT/US2017/052822
§ 371 (c)(1),
(2) Date: Mar. 21, 2019

(87) PCT Pub. No.: WO2018/057812
PCT Pub. Date: Mar. 29, 2018

(65) Prior Publication Data
US 2020/0017861 A1 Jan. 16, 2020

Related U.S. Application Data

(60) Provisional application No. 62/397,867, filed on Sep. 21, 2016.

(51) Int. Cl.
*C12N 15/62* (2006.01)
*C12Q 1/6897* (2018.01)
*C07H 21/04* (2006.01)

(52) U.S. Cl.
CPC .............. *C12N 15/62* (2013.01); *C07H 21/04* (2013.01); *C12Q 1/6897* (2013.01); *C12N 2310/20* (2017.05); *C12N 2310/3519* (2013.01)

(58) Field of Classification Search
CPC ................ C12N 15/62; C12N 2310/20; C12N 2310/3519; C07H 21/04; C12Q 1/6897
See application file for complete search history.

(56) References Cited

U.S. PATENT DOCUMENTS

| 2014/0004146 A1 | 1/2014 | Zhou et al. |
| 2016/0194625 A1 | 7/2016 | Hoge et al. |
| 2016/0253584 A1 | 9/2016 | Fan et al. |
| 2016/0258962 A1 | 9/2016 | Battaglia |
| 2020/0017861 A1 | 1/2020 | Blainey et al. |

FOREIGN PATENT DOCUMENTS

| WO | 2013174999 A1 | 11/2013 | |
| WO | 2014/047561 A1 | 3/2014 | |
| WO | 2014110509 A1 | 7/2014 | |
| WO | 2016145416 A2 | 9/2016 | |
| WO | WO-2016145416 A2 * | 9/2016 | ......... C12N 15/1075 |
| WO | 2018057812 A2 | 3/2018 | |

OTHER PUBLICATIONS

De Souza et al. The TAL Effector PthA4 Interacts with Nuclear Factors Involved in RNA-Dependent Processes Including a HMG Protein That Selectively Binds Poly(U) RNA. PLoS 2012. 7(2) e32305 (Year: 2012).*
Jouvenet et al. Imaging the interaction of HIV-1 genomes and Gag during assembly of individual viral particles PNAS, 2009. vol. 106 No. 45 19114-19119 (Year: 2009).*
Zhang et al. Gene expression profiling of non-polyadenylated RNA-seq across species Genomics Data 2 (2014) 237-241 (Year: 2014).*
Yang et al. Genomewide characterization of non-polyadenylated RNAs Genome Biology 2011, 12:R16 (Year: 2011).*
Thomas, "Invitation to Pay Additional Fees for PCT International Application No. PCT/US2017/052822", dated Nov. 27, 2017.
Thomas, "PCT International Search Report and Written Opinion issued in PCT/US2017/052822 dated Feb. 2, 2018", 1-17.
"Extended European Search Report issued in European Application No. 17853940.9", dated Sep. 30, 2020, 14 pages.
Kiyama, et al., "In Vitro Transcription of a Poly(dA)-Poly(dT)-Containing Sequence is Inhibited by Interaction between the Template and Its Transcripts", Nucleic Acids Research, vol. 24, No. 22, Nov. 1, 1996 (Nov. 1, 1996), pp. 4577-4583, XP055732821, 7 pages.
"European Office Action issued in European Application No. 17853940.9", dated Jun. 2, 2020, 11 pages.
"International Preliminary Report on Patentability issued in International Application No. PCT/US2017/052822", dated May 16, 2019, 9 pages.
Orioli, et al., "Widespread Occurrence of Non-canonical Transcription Termination by Human RNA Polymerase III", Nucleic Acids Research, vol. 39, No. 13, Mar. 17, 2011, 14 pages.
Picelli, et al., "Full-Length RNA-Seq from Single Cells using Smart-seq2", Nature Protocols,vol. 9, No. 1, Jan. 2, 2014, 171-181.

(Continued)

*Primary Examiner* — Scarlett Y Goon
*Assistant Examiner* — Tiffany Nicole Grooms
(74) *Attorney, Agent, or Firm* — F. Brent Nix, Esq.; Johnson, Marcou, Isaacs & Nix, LLC; Carin R. Miller, Esq.

(57) ABSTRACT

The present invention provides for methods to obtain multiple information-rich samples at different time points from the same cell while minimally disrupting the cell. The subject matter disclosed herein is generally related to nucleic acid constructs for continuous monitoring of live cells. Specifically, the subject matter disclosed herein is directed to nucleic acid constructs that encode a fusion protein and a construct RNA sequence that induce live cells to self-report cellular contents while maintaining cell viability. The present invention may be used to monitor gene expression in single cells while maintaining cell viability.

22 Claims, 18 Drawing Sheets

Specification includes a Sequence Listing.

(56) References Cited

OTHER PUBLICATIONS

Rulli, et al., "Selective and Nonselective Packaging of Cellular RNAs in Retrovirus Particles", Journal of Virology, The American Society for Microbiology, vol. 81, No. 12, Jun. 1, 2007, 6623-6631.
Siwiak, et al., "Transimulation-Protein Biosynthesis Web Service", PLoS One, Sep. 2013, vol. 8, Issue 9, Sep. 2013, 8 pages.
Sun, et al., "A New RNA Vaccine Platform Based on MS2 Virus-like Particles Produced in *Saccharomyces cerevisiae*", Biochemical and Biophysical Research Communications, vol. 407, 2011, 124-128.
Verma, Inderm. , "The Reverse Transcriptase", Biochimica et Biophysica Acta (BBA)—Reviews on Cancer, vol. 473, Issue 1, Mar. 21, 1977, 38 pages.
Yang, et al., "Decay Rates of Human mRNAs: Correlation with Functional Characteristics and Sequence Attributes", Genome Research, vol. 13, No. 8, Aug. 2003, 1863-1872.

* cited by examiner

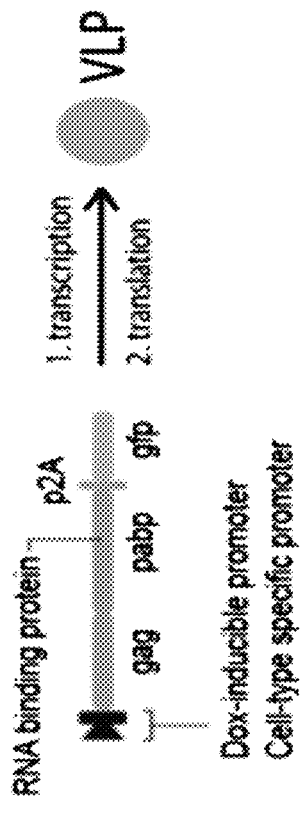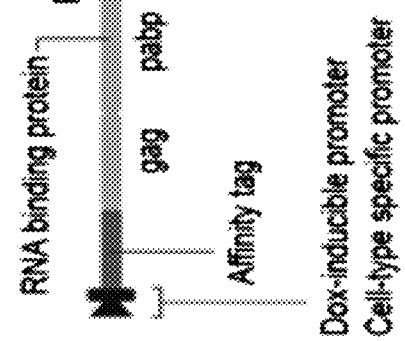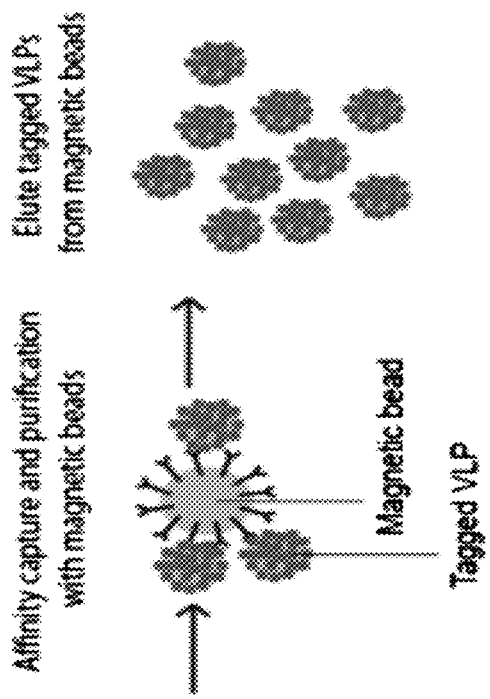
FIG. 6

| reporting unit scale | typical number of cells in reporting unit | sample collection time to accumulate 10 detected counts of a given mRNA, protein, or lipid species* example RNA species present at 1000 copies per cell (assume total of 200,000 mRNA/cell) | example protein species present at 0.05% in VLP sample | example lipid species present at 0.05% in VLP sample |
|---|---|---|---|---|
| Single Cell | 1 | hours | seconds | seconds |
| Tissue | 50,000 | seconds | very short | very short |
| Organ | 10,000,000 | very short | very short | very short |
| Organism | 1×10³³ | very short | very short | very short |
| Total molecules sampled per cell per hour | | 3,000 | 100,000 | 1,000,000 |
| estimated % of cell's production | | 10% | <1% | <1% |
| estimated analytical detection efficiency | | 10% | 0.1% | 0.1% |

* equivalent to assay time resolution for quantification with coefficient of variation ~30%

FIG. 10

SEQUENCE LISTING

<160> NUMBER OF SEQ ID NOS: 12

<210> SEQ ID NO 1
<211> LENGTH: 1590
<212> TYPE: DNA
<213> ORGANISM: Artificial Sequence
<220> FEATURE:
<223> OTHER INFORMATION: MLV gag

<400> SEQUENCE: 1

```
atgggccaga ctgttaccac tcccttaagt ttgaccttag gtcactggaa agatgtcgag    60
cggatcgctc acaaccagtc ggtagatgtc aagaagagac gttgggttac cttctgctct   120
gcagaatggc caacctttaa cgtcggatgg ccgcgagacg gcacctttaa ccgagacctc   180
atcacccagg ttaagatcaa ggtcttttca cctggcccgc atggacaccc agaccaggtc   240
ccctacatcg tgacctggga agccttggct tttgaccccc ctccctgggt caagcccttt   300
gtacacccta agcctccgcc tcctcttcct ccatccgccc cgtctctccc ccttgaacct   360
cctcgttcga ccccgcctcg atcctccctt tatccagccc tcactccttc tctaggcgcc   420
aaacctaaac ctcaagttct ttctgacagt ggggggccgc tcatcgacct acttacagaa   480
gaccccccgc ttataggga cccaagacca ccccttccg acaggacgg aaatggtgga    540
gaagcgaccc ctgcgggaga ggcaccggac ccctccccaa tggcatctcg cctacgtggg   600
agacgggagc ccctgtggc cgactccact acctcgcagg cattccccct ccgcgcagga   660
ggaaacggac agcttcaata ctggccgttc tcctcttctg acctttacaa ctggaaaaat   720
aataacccctt cttttttctga agatccaggt aaactgacag ctctgatcga gtctgttctc   780
atcacccatc agcccacctg gacgactgt cagcagctgt gggacctct gctgaccgga   840
gaagaaaaac aacgggtgct cttagaggct agaaaggcgg tgcgggcga tgatgggcgc   900
cccactcaac tgcccaatga agtcgatgcc gcttttcccc tcgagcgccc agactggat   960
tacaccaccc caggcaggtag gaaccaccta gtccactatc gccagttgct cctagcgggt  1020
ctccaaaacg cgggcagaag ccccaccaat ttggccaagg taaaaggaat aacacaaggg  1080
cccaatgagt ctccctcggc cttcctagag agacttaagg aagcctatcg caggtacact  1140
ccttatgacc ctgaggaccc agggcaagaa actaatgtgt ctatgtcttt catttggcag  1200
tctgccccag acattgggag aaagttagag aggttagaag atttaaaaaa caagacgctt  1260
ggagatttgg ttagagaggc agaaaagatc tttaataaac gagaaacccc ggaagaaaga  1320
gaggaacgta tcaggagaga aacagaggaa aaagaagaac gccgtaggac agaggatgag  1380
cagaaagaga aagaaagaga tcgtaggaga catagagaga tgagcaagct attggccact  1440
gtcgttagtg gacagaaaca ggatagacag ggaggagaac gaaggaggtc ccaactcgat  1500
cgcgaccagt gtgcctactg caaagaaaag gggcactggg ctaaagattg tcccaagaaa  1560
ccacgaggac ctcggggacc aagaccgcag                                   1590
```

<210> SEQ ID NO 2
<211> LENGTH: 1935
<212> TYPE: DNA
<213> ORGANISM: Artificial Sequence
<220> FEATURE:
<223> OTHER INFORMATION: PABPC4 - RNA binding protein fragment

<400> SEQUENCE: 2

```
atgaacgctg cggccagcag ctaccccatg gcctccctgt acgtgggcga cctgcattcg    60
gacgtcaccg aggccatgct gtacgaaaag ttcagccccg cggggcctgt gctgtccatc   120
```

```
cgggtctgcc gcgatatgat caccagccgc tccctgggct atgcctacgt caacttccag    180
cagccggccg acgctgagcg ggctttggac accatgaact tgatgtgat taagggaaag     240 ccaatccgca tcatgtggtc tcagagggat ccctctttga gaaatctgg tgtgggaaac     300 gtcttcatca agaacctgga caaatctata gataacaagg cactttatga tactttttct   360
gcttttggaa acatactgtc ctgcaaggtg gtgtgtgatg agaacggctc taagggttat   420
gcctttgtcc acttcgagac ccaagaggct gccgacaagg ccatcgagaa gatgaatggc   480
atgctcctca tgaccgcaa agtatttgtg ggcagattca agtctcgcaa agagcgggaa    540
gctgagcttg gagccaaagc caaggaattc accaatgttt atatcaaaaa ctttggggaa   600
gaggtggatg atgagagtct gaaagagcta ttcagtcagt ttggtaagac cctaagtgtc   660
aaggtgatga gagatcccaa tgggaaatcc aaaggctttg gctttgtgag ttacgaaaaa   720
cacgaggatg ccaataaggc tgtggaagag atgaatggaa agaaataag tggtaaaatc    780 atatttgtag gccgtgcaca aaagaaagta gaacggcagg cagagttaaa acggaaattt   840
gaacagttga acaggagag aattagtcga tatcaggggg tgaatctcta cattaagaac   900
ttggatgaca ctattgatga tgagaaatta aggaaagaat tttctccttt tggatcaatt   960
accagtgcta aggtaatgct ggaggatgga agaagcaaag ggtttggctt cgtctgcttc   1020
tcatctcctg aagaagcaac caaagcagtc actgagatga atggacgcat tgtgggctcc   1080
aagccactat atgttgccct ggcccagagg aaggaagaga gaaaggctca cctgaccaac   1140
cagtatatgc aacgagtggc tggaatgaga gcacttcctg ccaatgccat cttaaatcag   1200
ttccagcctg cagcgggtgg ctactttgtg ccagcagtcc cacaggctca gggaaggcct   1260
ccatattata cacctaacca gttagcacag atgaggccta atccacgctg gcagcaaggt   1320
gggagacctc aaggcttcca aggaatgcca agtgctatac gccagtctgg gcctcgtcca   1380
actcttcgcc atctggctcc aactgggtct gagtgcccgg accgcttggc tatggacttt   1440
ggtggggctg gtgccgccca gcaagggctg actgacagct gccagtctgg aggcgttccc   1500
acagctgtgc agaacttagc gccacgcgct gctgttgctg ctgctgctcc ccgggctgtt   1560 gcccctaca aatacgcctc cagtgtccgc agccctcatc ctgccataca gcctctgcag   1620 gcacccagc ctgcggtcca tgtgcagggg caggagccac tgactgcctc catgctggct   1680
gcagcacccc cccaggaaca gaagcagatg ctgggagaac gcttgttccc actcatccaa   1740
acaatgcatt caaatctggc tgggaagatc acgggaatgc tgctggagat agacaactct   1800
gagctgctgc acatgttaga gtcccccgag tctctccgct ccaaggtgga tgaagctgta   1860
gcagttctac aggctcatca tgccaagaaa gaagctgccc agaaggtggg cgctgttgct   1920
gctgctacct cttag                                                    1935
```

<210> SEQ ID NO 3
<211> LENGTH: 387
<212> TYPE: DNA
<213> ORGANISM: Artificial Sequence
<220> FEATURE:
<223> OTHER INFORMATION: MS2 (N55K) - RNA binding protein fragment

<400> SEQUENCE: 3

```
gcttcaaact ttactcagtt cgtgctcgtg acaatggtg ggacagggga tgtgacagtg     60
gctccttcta atttcgctaa tggggtggca gagtggatca gctccaactc acggagccag    120
gcctacaagg tgacatgcag cgtcaggcag tctagtgccc agaagagaaa gtataccatc    180
```

```
aaggtggagg tccccaaagt ggctacccag acagtgggcg gagtcgaact gcctgtcgcc    240
gcttggaggt cctacctgaa catggagctc actatcccaa ttttcgctac caattctgac    300
tgtgaactca tcgtgaaggc aatgcagggg ctcctcaaag acggtaatcc tatcccttcc    360
gccatcgccg ctaactcagg tatctac                                       387
```

<210> SEQ ID NO 4
<211> LENGTH: 4137
<212> TYPE: DNA
<213> ORGANISM: Artificial Sequence
<220> FEATURE:
<223> OTHER INFORMATION: dCas9 - - RNA binding protein fragment

<400> SEQUENCE: 4

```
atgagcccca agaagaagag aaaggtggag gccagcgaca agaagtacag catcggcctg    60
gccatcggca ccaactctgt gggctgggcc gtgatcaccg acgagtacaa ggtgcccagc   120
aagaaattca aggtgctggg caacaccgac cggcacagca tcaagaagaa cctgatcgga   180
gccctgctgt tcgacagcgg cgaaacagcc gaggccaccc ggctgaagag aaccgccaga   240
agaagataca ccagacggaa gaaccggatc tgctatctgc aagagatctt cagcaacgag   300
atggccaagg tggacgacag cttcttccac agactggaag agtccttcct ggtggaagag   360
gataagaagc acgagcggca cccatcttc ggcaacatcg tggacgaggt ggcctaccac    420
gagagtaccc ccaccatcta ccacctgaga aagaaactgg tggacagcac cgacaaggcc   480
gacctgcggc tgatctatct ggccctggcc cacatgatca agttccgggg ccacttcctg   540
atcgagggcg acctgaaccc cgacaacagc gacgtggaca gcctgttcat ccagctggtg   600
cagacctaca accagctgtt cgaggaaaac cccatcaacg ccagcggcgt ggacgccaag   660
gccatcctgt ctgccagact gagcaagagc agacggctgg aaaatctgat cgcccagctg   720
cccggcgaga agaagaatgg cctgttcggc aacctgattg ccctgagcct gggcctgacc   780
cccaacttca gagcaacttt cgacctggcc gaggatgcca aactgcagct gagcaaggac   840
acctacgacg acgacctgga caacctgctg gcccagatcg gcgaccagta cgccgacctg   900
tttctggccg ccaagaacct gtccgacgcc atcctgctga gcgacatcct gagagtgaac   960
accgagatca ccaaggcccc cctgagcgcc tctatgatca agagatacga cgagcaccac   1020
caggacctga ccctgctgaa agctctcgtg cggcagcagc tgcctgagaa gtacaaagag   1080
attttcttcg accagagcaa gaacggctac gccggctaca ttgacggcgg agccagccag   1140
gaagagttct acaagttcat caagcccatc ctggaaaaga tggacggcac cgaggaactg   1200
ctcgtgaagc tgaacagaga ggacctgctg cggaagcagc ggaccttcga caacggcagc   1260
atcccccacc agatccacct gggagagctg cacgccattc tgcggcggca ggaagatttt   1320
tacccattcc tgaaggacaa ccgggaaaag atcgagaaga tcctgacctt ccgcatcccc   1380
tactacgtgg gccctctggc caggggaaac agcagattcg cctggatgac cagaaagagc   1440
gaggaaacca tcaccccctg gaacttcgag gaagtggtgg acaagggcgc ttccgcccag   1500
agcttcatcg agcggatgac caacttcgat aagaacctgc caacgagaa ggtgctgccc   1560 aagcacagcc tgctgtacga gtacttcacc gtgtataacg agctgaccaa agtgaaatac   1620
gtgaccgagg gaatgagaaa gccggccttc ctgagcggcg agcagaaaaa ggccatcgtg   1680
gacctgctgt tcaagaccaa ccggaaagtg accgtgaagc agctgaaaga ggactacttc   1740
aagaaaatcg agtgcttcga ctccgtggaa atctccggcg tggaagatcg gttcaacgcc   1800
tccctgggca cataccacga tctgctgaaa attatcaagg acaaggactt cctggacaat   1860
```

```
gaggaaaacg aggacattct ggaagatatc gtgctgaccc tgacactgtt tgaggacaga    1920
gagatgatcg aggaacggct gaaaacctat gcccacctgt tcgacgacaa agtgatgaag    1980
cagctgaagc ggcggagata caccggctgg ggcaggctga gccggaagct gatcaacggc    2040
atccgggaca agcagtccgg caagacaatc ctggatttcc tgaagtccga cggcttcgcc    2100
aacagaaact tcatgcagct gatccacgac gacagcctga cctttaaaga ggacatccag    2160
aaagcccagg tgtccggcca gggcgatagc ctgcacgagc acattgccaa tctgccggc    2220 agccccgcca ttaagaaggg catcctgcag acagtgaagg tggtggacga gctcgtgaaa    2280
gtgatgggcc ggcacaagcc cgagaacatc gtgatcgaaa tggccagaga gaaccagacc    2340
acccagaagg gacagaagaa cagccgcgag agaatgaagc ggatcgaaga gggcatcaaa    2400
gagctgggca gccagatcct gaaagaacac cccgtggaaa acacccagct gcagaacgag    2460
aagctgtacc tgtactacct gcagaatggg cgggatatgt acgtggacca ggaactggac    2520
atcaaccggc tgtccgacta cgatgtggac gctatcgtgc ctcagagctt tctgaaggac    2580
gactccatcg acaacaaggt gctgaccaga agcgacaaga accggggcaa gagcgacaac    2640
gtgccctccg aagaggtcgt gaagaagatg aagaactact ggcggcagct gctgaacgcc    2700
aagctgatta cccagagaaa gttcgacaat ctgaccaagg ccgagagagg cggcctgagc    2760
gaactggata aggccggctt catcaagaga cagctggtgg aaacccggca gatcacaaag    2820
cacgtggcac agatcctgga ctcccggatg aacactaagt acgacgagaa tgacaagctg    2880
atccgggaag tgaaagtgat cacccctgaag tccaagctgg tgtccgattt ccggaaggat    2940
ttccagtttt acaaagtgcg cgagatcaac aactaccacc acgcccacga cgcctacctg    3000
aacgccgtcg tgggaaccgc cctgatcaaa aagtaccctaa agctggaaag cgagttcgtg    3060
tacggcgact acaaggtgta cgacgtgcgg aagatgatcg ccaagagcga gcaggaaatc    3120
ggcaaggcta ccgccaagta cttcttctac agcaacatca tgaactttt caagaccgag    3180 attaccctgg ccaacggcga gatccggaag cggcctctga tcgagacaaa cggcgaaacc    3240
ggggagatcg tgtgggataa gggccgggat tttgccaccg tgcggaaagt gctgagcatg    3300
ccccaagtga atatcgtgaa aaagaccgag gtgcagacag gcggcttcag caaagagtct    3360
atcctgccca gaggaacag cgataagctg atcgccagaa agaaggactg ggaccctaag    3420
aagtacggcg gcttcgacag ccccaccgtg gcctattctg tgctggtggt ggccaaagtg    3480
gaaaagggca gtccaagaa actgaagagt gtgaaagagc tgctggggat caccatcatg    3540
gaaagaagca gcttcgagaa gaatcccatc gactttctgg aagccaaggg ctacaaagaa    3600
gtgaaaaagg acctgatcat caagctgcct aagtactccc tgttcgagct ggaaaacggc    3660
cggaagagaa tgctggcctc tgccggcgaa ctgcagaagg gaaacgaact ggccctgccc    3720
tccaaatatg tgaacttcct gtacctggcc agccactatg agaagctgaa gggctcccc   3780 gaggataatg agcagaaaca gctgtttgtg gaacagcaca gcactacct ggacgagatc    3840 atcgagcaga tcagcgagtt ctccaagaga gtgatcctgg ccgacgctaa tctggacaaa    3900
gtgctgtccg cctacaacaa gcaccggat aagcccatca gagagcaggc cgagaatatc    3960
atccacctgt ttaccctgac caatctggga gcccctgccg ccttcaagta ctttgacacc    4020
accatcgacc ggaagaggta caccagcacc aaagaggtgc tggacgccac cctgatccac    4080
cagagcatca ccggcctgta cgagacacgg atcgacctgt ctcagctggg aggcgac      4137
```

<210> SEQ ID NO 5

```
<211> LENGTH: 66
<212> TYPE: DNA
<213> ORGANISM: Artificial Sequence
<220> FEATURE:
<223> OTHER INFORMATION: p2A protein domain

<400> SEQUENCE: 5
ggatccggcg caacaaactt ctctctgctg aaacaagccg agatgtcga agagaatcct      60 ggaccg                                                                66

<210> SEQ ID NO 6
<211> LENGTH: 711
<212> TYPE: DNA
<213> ORGANISM: Artificial Sequence
<220> FEATURE:
<223> OTHER INFORMATION: YFP  protein domain

<400> SEQUENCE: 6
agcaagggcg aggagctgtt caccggggtg gtgcccatcc tggtcgagct ggacggcgac      60
gtaaacggcc acaagttcag cgtgtccggc gagggcgagg gcgatgccac ctacggcaag     120
ctgaccctga agttcatctg caccaccggc aagctgcccg tgccctggcc caccctcgtg     180
accaccttcg gctacggcct gcagtgcttc gcccgctacc ccgaccacat gaagcagcac     240
gacttcttca gtccgccat gcccgaaggc tacgtccagg agcgcaccat cttcttcaag     300
gacgacggca actacaagac ccgcgccgag gtgaagttcg agggcgacac cctggtgaac     360
cgcatcgagc tgaagggcat cgacttcaag gaggacggca acatcctggg cacaagctg     420 gagtacaact acaacagcca caacgtctat atcatggccg acaagcagaa gaacggcatc     480
aaggtgaact tcaagatccg ccacaacatc gaggacggca gcgtgcagct cgccgaccac     540
taccagcaga cacccccat cggcgacggc cccgtgctgc tgcccgacaa ccactacctg     600
agctaccagt ccgccctgag caaagacccc aacgagaagc gcgatcacat ggtcctgctg     660
gagttcgtga ccgccgccgg gatcactctc ggcatggacg agctgtacaa g             711

<210> SEQ ID NO 7
<211> LENGTH: 21
<212> TYPE: DNA
<213> ORGANISM: Artificial Sequence
<220> FEATURE:
<223> OTHER INFORMATION: GS6 linker

<400> SEQUENCE: 7
ggatcaggat caggatcagg a                                                21

<210> SEQ ID NO 8
<211> LENGTH: 204
<212> TYPE: DNA
<213> ORGANISM: Artificial Sequence
<220> FEATURE:
<223> OTHER INFORMATION: bGH pA terminator

<400> SEQUENCE: 8
cgactgtgcc ttctagttgc cagccatctg ttgtttgccc ctcccccgtg ccttccttga      60
ccctggaagg tgccactccc actgtccttt cctaataaaa tgaggaaatt gcatcgcatt     120
gtctgagtag gtgtcattct attctggggg gtggggtggg gcaggacagc aaggggagg     180 attgggaaga caatagcagg catg                                            204

<210> SEQ ID NO 9
<211> LENGTH: 20
```

```
<212> TYPE: DNA
<213> ORGANISM: Artificial Sequence
<220> FEATURE:
<223> OTHER INFORMATION: spacer

<400> SEQUENCE: 9
ctgcaggtcg actctagaaa                                              20

<210> SEQ ID NO 10
<211> LENGTH: 19
<212> TYPE: DNA
<213> ORGANISM: Artificial Sequence
<220> FEATURE:
<223> OTHER INFORMATION: MS2 hairpin

<400> SEQUENCE: 10
acatgaggat cacccatgt                                               19

<210> SEQ ID NO 11
<211> LENGTH: 25
<212> TYPE: DNA
<213> ORGANISM: Artificial Sequence
<220> FEATURE:
<223> OTHER INFORMATION: Smartseq2 handle

<400> SEQUENCE: 11
aagcagtggt atcaacgcag agtac                                        25

<210> SEQ ID NO 12
<211> LENGTH: 24
<212> TYPE: DNA
<213> ORGANISM: Artificial Sequence
<220> FEATURE:
<223> OTHER INFORMATION: polyA capture

<400> SEQUENCE: 12
ttgttgttgt tgttgttgtt tttt                                         24
```

CONSTRUCTS FOR CONTINUOUS MONITORING OF LIVE CELLS

CROSS-REFERENCE TO RELATED APPLICATIONS

This application is a 35 U.S.C. § 371 national stage of International Application No. PCT/US17/52822 filed on Sep. 21, 2017, which claims the benefit of U.S. Provisional Application No. 62/397,867 filed on Sep. 21, 2016. The entire contents of the above-identified application are fully incorporated herein by reference.

TECHNICAL FIELD

The subject matter disclosed herein is generally related to nucleic acid constructs for continuous monitoring of live cells. Specifically, the subject matter disclosed herein is directed to nucleic acid constructs that encode a fusion protein and a construct RNA sequence that induce live cells to self-report cellular contents while maintaining cell viability.

REFERENCE TO AN ELECTRONIC SEQUENCE LISTING

The contents of the electronic sequence listing ("BROD-0821US_ST25.txt;" 14 KB and created on Aug. 19, 2020) is herein incorporated by reference in its entirety.

BACKGROUND

Single-cell gene expression (SCGE) profiling is an important analytical technique for the study of mammalian cells. The ability to obtain highly resolved molecular phenotypes directly from individual cells is transforming the way cell states are defined, cell circuitry is understood, and how cellular responses to environmental cues are studied. There is tremendous interest in moving beyond static snapshots of SCGE in cell suspensions to understand how SCGE profiles change over time. Technology that reports the internal state and functional history of cells within tissues would enable novel insight into dynamic biological processes. Current SCGE profiling technology addresses static heterogeneity (e.g. a snapshot of differences among single-cells). However, dynamic signaling processes (Cai L, Nature 2008; Yosef N, Cell 2011; Yosef N, Nature 2013) and transitions in cell type and function over time are crucial to cellular biology and organism-level function. Enabling the comprehensive study of dynamic processes at the single-cell level is of intense interest, but tools for non-destructive in situ analysis are currently lacking. New methods are needed to obtain multiple information-rich samples at different time points from the same cell while minimally disrupting the cell.

SUMMARY

In one aspect, the embodiments described herein are directed to nucleic acid constructs that encode a fusion protein and a construct RNA sequence. The fusion protein may comprise a secretion-inducing domain and a construct RNA capture domain. When expressed in live cells the secretion domain induces the cell to export samples of cellular content that can be isolated and analyzed while maintaining cell viability. In certain example embodiments, the secretion domain facilitates the formation of an export compartment capable of packaging cellular contents and exporting those cellular contents from the cell. The construct RNA capture domain of the fusion protein is one member of a binding pair that binds a corresponding RNA retrieval element on the expressed construct RNA sequence. The construct RNA sequence comprises a construct RNA retrieval element and a cellular RNA capture element. The construct RNA sequence may further comprise a barcode. The construct RNA retrieval element is recognized and bound by the construct RNA capture domain of the fusion protein. The cellular RNA capture domain hybridizes to cellular RNA. Binding of the construct RNA sequence/cellular RNA complex by the construct RNA capture element of the fusion protein results in export of the construct RNA sequence/cellular RNA complex in association with the secretion-inducing domain of the fusion protein. Thus, capture of cellular RNA by the construct RNA sequence enables export of the captured cellular RNA in association with the secretion-inducing domain of the fusion protein. In certain example embodiments, the secretion-inducing domain is a viral capsid or coat protein. In certain example embodiments, the secretion-inducing domain comprises a Gag protein or a functional fragment thereof. In certain example embodiments, the construct RNA capture domain of the fusion protein is a MS2 coat protein and the construct RNA retrieval element of the construct RNA comprises a sequence encoding a MS2 hairpin. In certain example embodiments, the construct RNA capture domain of the fusion protein is dCas9 and the construct RNA retrieval element of the construct RNA is a dCas9 binding loop.

In certain example embodiments, the RNA construct may further comprise a barcode, and a poly U sequence or a sequence comprising a (UUG)n motif for capture of cellular RNA. The barcode comprises a randomized sequence unique to the construct and therefore to the cell or cell population the construct is delivered to. Thus, in certain example embodiments, all cellular RNA captured by the RNA construct and exported from the cell via the fusion protein will have the same barcode thereby identifying all cellular RNA exported from the same cell.

The nucleic acid constructs described herein may further comprise an inducible promoter to control expression of the fusion protein, and/or construct RNA sequence. In certain example embodiments, the promoter may be a tissue or cell-specific promoter. The nucleic acid constructs described herein may further comprise a steric linker. The steric linker may be located on a N-terminus of the secretion-inducing protein or between the secretion-inducing domain and the construct RNA capture domain and may control the rate of secretion, the size of export compartments formed by the secretion-inducing protein, or both. The nucleic acid constructs described herein may further encode a fusion protein that includes an affinity tag for subsequent isolation and enrichment of the fusion protein and/or export compartments formed by the fusion protein. Further, the nucleic acids constructs may encode a detectable self-reporting molecule that can be used to confirm successful delivery and expression of the nucleic acid constructs described herein. In certain example embodiments, the detectable self-reporting molecule may be a cleavable self-reporting molecule that can be cleaved from the RNA construct after expression.

In another aspect, the embodiments disclosed herein comprise methods for continuous monitoring of live cells comprising delivering into a cell a nucleic acid construct described herein. The nucleic acid construct is expressed, for example, via an inducible promoter. Cellular RNA, such as mRNA or microRNA, is captured by hybridization to the cellular RNA capture element of the construct RNA sequence. The captured cellular RNA is then exported from the cell by binding of the construct RNA capture domain of the fusion protein to the retrieval element of the construct RNA sequence such that the construct RNA sequence—and bound cellular RNA—are exported from the cell in association with secretion inducing domain of the cellular protein. The exported fusion protein/construct RNA sequence/cellular RNA complex may then be isolated.

In certain example embodiments, the method further comprises generating a RNA-DNA duplex by reverse transcribing the captured cellular RNA using the construct RNA sequence as a primer for reverse transcription. A DNA-DNA duplex is then generated by converting the construct RNA sequence to a corresponding DNA sequence with second strand synthesis using a DNA primer. The DNA-DNA duplex is then used to generate a sequencing library for sequencing using, for example, a NGS sequencing platform. Sequencing of the DNA-DNA duplex library identifies the transcript and—via the barcode information—the cell of origin for each transcript thereby enabling continuous single-cell gene expression analysis.

In certain example embodiments, a nucleic acid construct for barcoding cellular components, such as expressed RNAs, comprises a barcode and a cellular RNA capture element. In certain example embodiments, the cellular RNA capture element is a poly(U) or $(UUG)_n$ motif. In certain example embodiments, the nucleic acid construct may further comprise a filter sequence that helps identify the barcode sequence in downstream sequencing reads. In certain example embodiments, the nucleic acid construct may comprise an adapter sequence that provides a complementary binding site for a reverse transcription or amplification primer. In certain other example embodiments, the nucleic acid construct may further comprise a sequencing primer binding site that is complementary to one or more sequencing primers used in downstream sequencing reactions. The nucleic acid constructs described in this paragraph may be used as the construct RNA sequence in relation to the self-reporting export compartment embodiments discussed above.

In another aspect, a method for labeling molecular components of cells according to cell or origin comprises expressing any of the above disclosed nucleic acid constructs in one or more cells, wherein the expressed nucleic acid construct comprises a barcode that is unique to an individual cell or cell lineage, capturing cellular RNA expressed in the one or more cells by binding of the cellular RNA via the cellular RNA capture element of the expressed construct sequence and incorporating the barcode of the expressed nucleic acid construct to the captured cellular RNA to generate barcoded cellular RNA. Barcoded RNA refer to directly barcoded RNAs as well as single and double stranded copies made from the original cellular RNA such as those shown in FIGS. 12-15. The barcode may be attached by ligation of the nucleic acid construct to the cellular RNA by RNA-RNA ligation, by priming first and/or second strand synthesis of the captured cellular RNA using the expressed nucleic acid construct. Barcoded RNA may be further amplified, for example, by RNA-dependent RNA synthesis, PCR, or linear DNA amplification.

In another aspect, the embodiments disclosed herein comprise vectors comprising the nucleic acid constructs described herein. In certain example embodiments, the vectors are viral vectors. In certain other example embodiments, the vectors are non-viral vectors.

In another aspect, embodiments disclosed herein include kits comprising the nucleic acid constructs and/or vectors described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 6—is a schematic of an example construct further encoding an affinity tag for subsequent isolation and enrichment of expressed VLPs in accordance with certain example embodiments.

FIG. 10—is a table showing projected achievable time resolution of gene expression using the constructs described herein.

DETAILED DESCRIPTION OF THE EXAMPLE EMBODIMENTS

General Definitions

Figure 1:
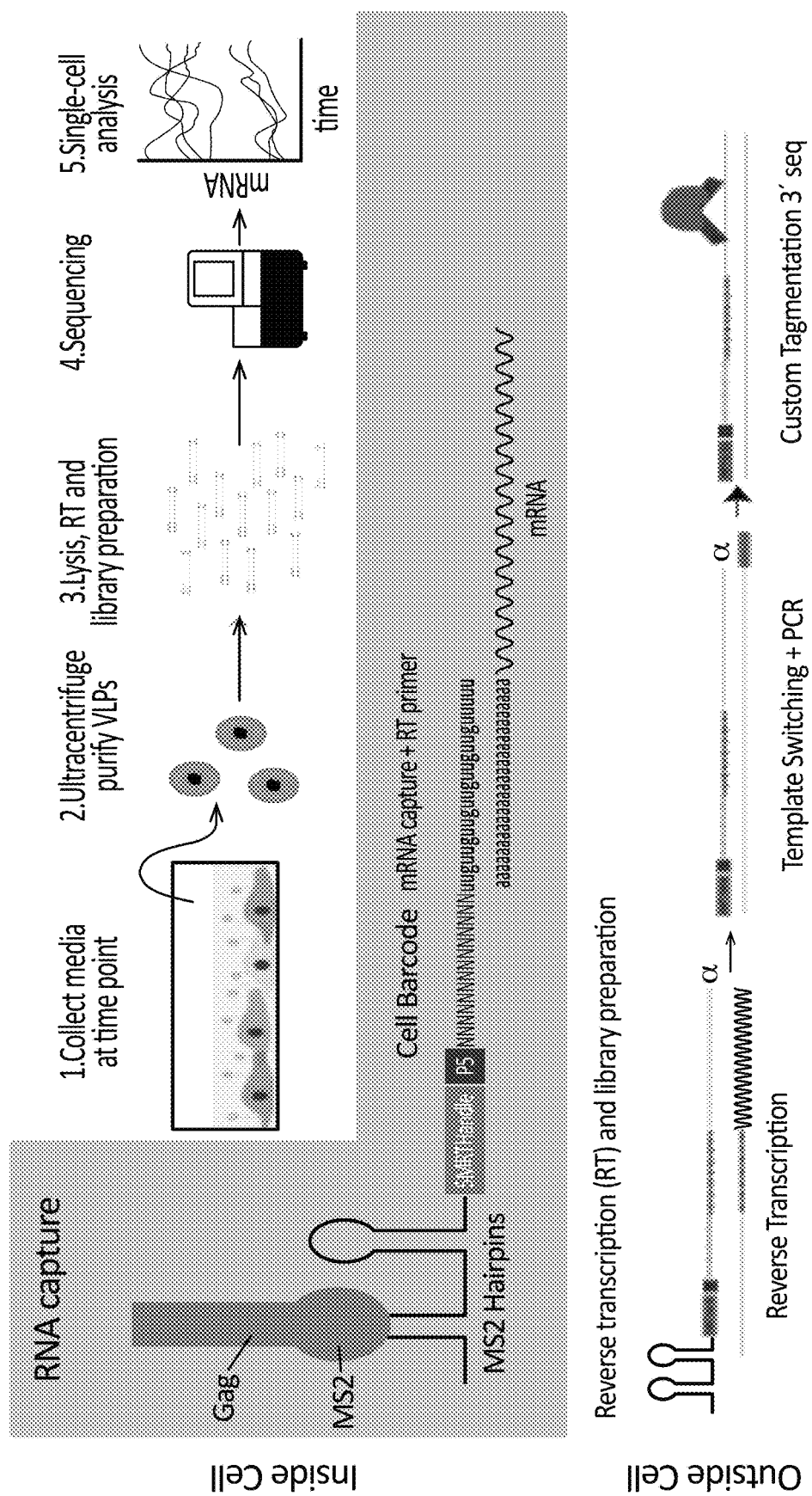
FIG. 1—is a schematic depicting a method for continuous single-cell gene expression analysis of live cells, in accordance with certain example embodiments.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +1-1% or less, and +1-0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide nucleic acid constructs and methods of use thereof that induce a live cell to self-report sub-samples of cellular content. The sampling can be general or can be targeted to a particular class of molecules or to specific types of molecules. The constructs facilitate generation of a read-out for high-throughput screens by combining engineered export with simple bulk sample and sample processing. Live cell sampling enables time course measurements and expands, for example, the applicability of transcriptional profiles obtained by single-cell gene expression analysis. The constructs may further comprise steric linkers, inducible promoters, detectable self-reporting molecules, and affinity elements as discussed in further detail below. When introduced into live cells the constructs disclosed herein enable live cell sampling of cellular contents while maintaining cell viability. Cellular contents may include nuclear as well as cytosolic contents. In addition, the nucleic acid constructs and methods further comprise the use of nucleic acid barcodes that tag each transcript molecule with a cell-identifying barcode, adding single-cell transcriptomic analysis to the self reporting approach disclosed herein.

Nucleic Acid Constructs

In certain example embodiments, the nucleic acid constructs comprise a nucleic acid sequence encoding a fusion protein and a construct RNA sequence. The fusion protein comprises a secretion-inducing domain and a construct RNA capture domain.

A secretion-inducing protein may comprise a polypeptide that when expressed induces a cell to export cellular contents in association with the secretion-inducing protein. As used herein, and in the context of proteins encoded by the nucleic acid constructs described herein, a "protein" may refer to the full length sequence of the protein or only that portion of the protein that is necessary for the function for which the full length protein is otherwise expressed. In certain example embodiments, the secretion-inducing protein is an export compartment protein. An export compartment protein may be any protein that self-assembles upon expression in a cell into an export compartment. In certain example embodiments, an export compartment is a spherical macromolecular assembly comprising a protein inner layer and an outer lipid containing membrane, with at least the export-compartment protein forming the inner protein layer. In certain example embodiments, the export compartment protein may only form a partial export compartment while retaining the ability to associate with and export the targeted cellular contents. In certain example embodiments, the export compartment protein is a viral export compartment protein that forms virus-like particles. Regarding embodiments that use viral export compartment proteins, the terms export compartment and virus-like particle (VLP) may be used interchangeably. Example viral export compartment proteins may include viral capsid proteins. In certain example embodiments, the viral capsid protein is a viral Gag protein. In certain example embodiments, the viral Gag protein is a lentivirus Gag protein. In certain example embodiments, the export compartment protein is encoded by a nucleic acid sequence of SEQ ID NO: 1.

The construct RNA capture domain may be a protein or peptide that recognizes and binds a retrieval element of the construct RNA sequence after expression of the construct RNA sequence in the cell. The construct RNA capture domain of the fusion protein may comprise any protein or peptide that recognizes and selectively binds a target sequence or structural feature of the expressed construct RNA sequence. In certain example embodiments, the construct RNA capture domain may be a protein or peptide that recognizes and binds RNA secondary structural features, such as but not limited to, hairpins. In certain example embodiments, the construct RNA capture domain comprises a dCas9 protein and the retrieval element of the construct RNA sequence may comprise a sequence encoding the dCas9-binding hairpin. In certain other example embodiments, the construct RNA capture domain of the fusion protein may be a viral capsid protein that binds a sequence or structural feature of the corresponding viral genome. For example, the construct RNA capture domain may be a MS2 coat protein and the retrieval element of the construct RNA sequence may comprise a RNA sequence defining a MS2 hairpin. In certain example embodiments, the construct RNA capture domain comprises a protein encoded by SEQ ID NO: 2, SEQ ID NO: 3, or SEQ ID NO: 4, or functional equivalents thereof. In certain example embodiments, the retrieval element of the construct RNA sequence comprises SEQ ID NO: 10.

The construct RNA sequence comprises a retrieval element and a cellular RNA capture element. The construct RNA may also further comprise a reverse transcription primer binding site and a barcode. The construct RNA retrieval element is recognized and bound by the construct RNA capture domain on the fusion protein such that the construct RNA is exported from the cell in association with the secretion-inducing protein. In certain example embodiments, the secretion-inducing protein is an export compartment protein and the construct RNA is packaged within the export compartment formed by the fusion protein. In certain example embodiments, the cellular RNA capture element hybridizes to cellular RNA such that the bound cellular RNA is packaged inside the export compartment with the construct RNA.

The cellular RNA capture element of the construct RNA sequence binds target RNAs in the cell. The cellular RNA capture element may bind target RNAs in an unbiased manner. For example, the cellular RNA capture element may be a poly-U sequence. In certain example embodiments, the poly-U sequence is approximately 15 to approximately 50 nucleotides long. In certain other example embodiments, the cellular RNA capture element may comprise a (UUG)n motif, wherein "n" may range from approximately 1 to approximately 20. In certain example embodiments, the cellular RNA capture element may comprise a sequence that can hybridize to a specific target RNA species, such as specific mRNA transcript. In certain example embodiments, the cellular RNA capture element comprises SEQ ID NO: 12.

The construct RNA sequence may further include a barcode. A barcode is generated by sequentially attaching two or more detectable oligonucleotide tags to each other. As used herein, a "detectable oligonucleotide tag" is an oligonucleotide that can be detected by sequencing of its nucleotide sequence and/or by hybridization to detectable moieties such as optically labeled probes. The oligonucleotide tags that make up a barcode are typically randomly selected from a diverse set of oligonucleotide tags. For example, an oligonucleotide tag may be selected from a set A, B, C, and D, with each set comprising random sequences of a particular size. An oligonucleotide tag is first selected from set A, then a second oligonucleotide tag is selected from set B and concatenated to the oligonucleotide from set A. The process is repeated for sets C and D such that an oligonucleotide tag from C is concatenated to AB and an oligonucleotide tag from D is concatenated to ABC. The particular sequence selected from each set and the order in which the oligonucleotides are concatenated define a unique barcode. Methods for generating barcodes for use in the constructs disclosed herein are described, for example, in International Patent Application Publication No. WO/2014/047561. In certain example embodiments, the barcodes are approximately 10 to approximately 40 nucleotides long. In certain example embodiments, the barcodes comprise 2, 3, 4, 5, 6, 7, 8, 9, or 10 distinct ordered positions. In certain example embodiments, the barcode of each construct is unique to that construct or sub-set of constructs such that delivery of that construct or sub-set of constructs is unique to that cell or population of cells. For example, a first cell or population of cells may be transduced with a first construct or set of constructs comprising a first barcode, and a second cell or second population of cells may be transduced with a second construct of set of constructs comprising a second barcode, such that sequencing libraries derived from exported cellular RNA from a particular cell or cell population will include the same unique barcode, thereby identifying those cellular RNAs as originating from the same cell or same cell population.

In certain example embodiments, the nucleic acid constructs only comprise a construct RNA sequence and may be used independently to barcode cellular components with origin-specific barcodes without use of the fusion proteins and self-reporting export as discussed above. These nucleic acid constructs encode a barcode and a cellular RNA capture element as described above. In certain example embodiments, the construct RNA sequence may further comprise a filter sequence. The filter sequence is a defined and searchable nucleic acid sequence set at a fixed distance from all barcodes or other unique molecular identifiers, thus enabling detection of barcodes and unique molecular identifiers in downstream sequencing data as further described below. The construct RNA sequence may also further comprise an adapter sequence. The adapter sequence defines a nucleic acid sequence that is complementary and enables binding of downstream amplification and/or sequencing primers as described further below.

General Construct Elements

Figure 5:
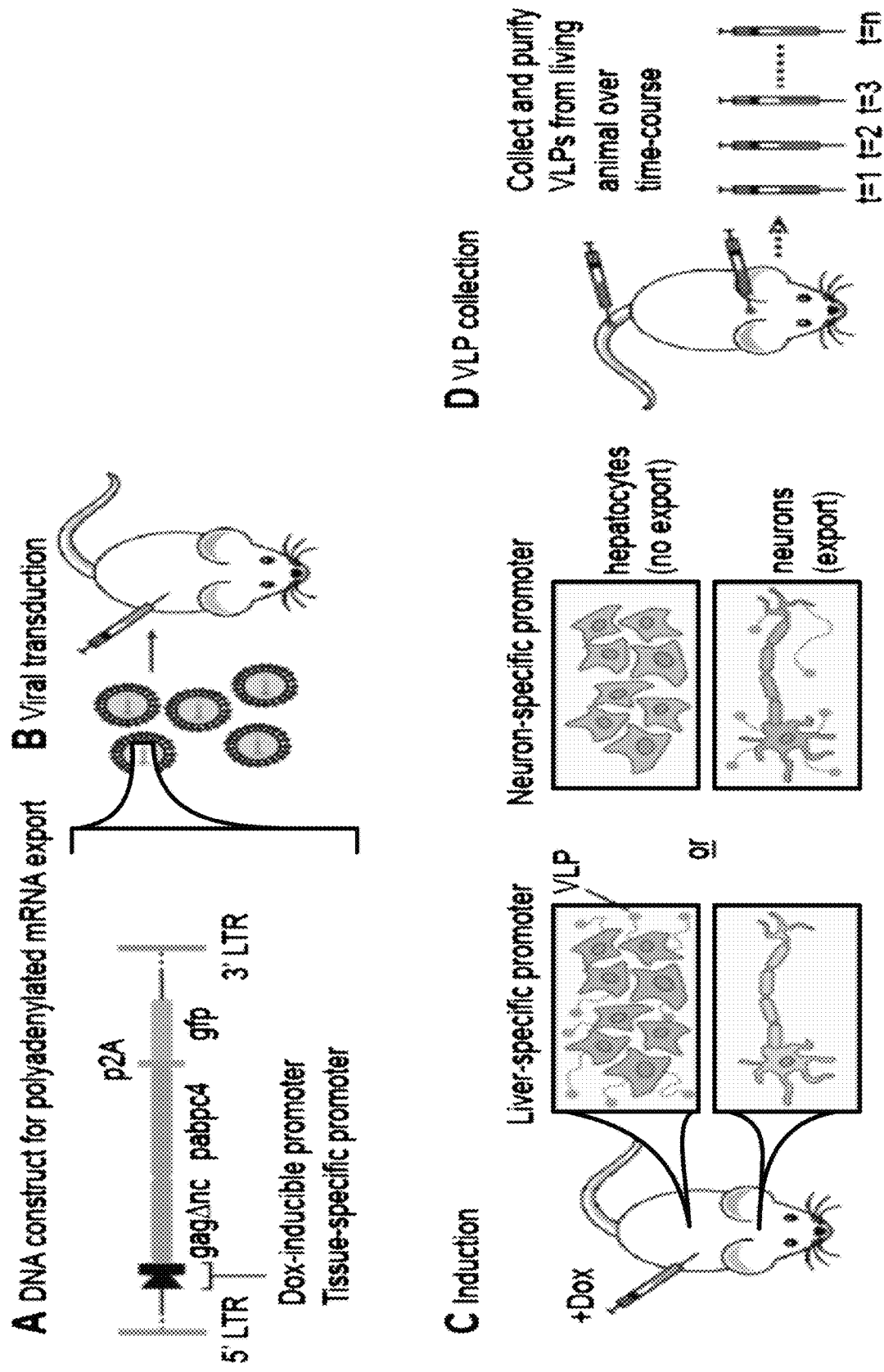
FIG. 5—is a schematic showing an example construct comprising a tissue-specific promoter, a dox-inducible promoter or a combination of the two, a linker, and labile self-reporting molecule and the use of said construct in accordance with certain example embodiments.
Figure 7:
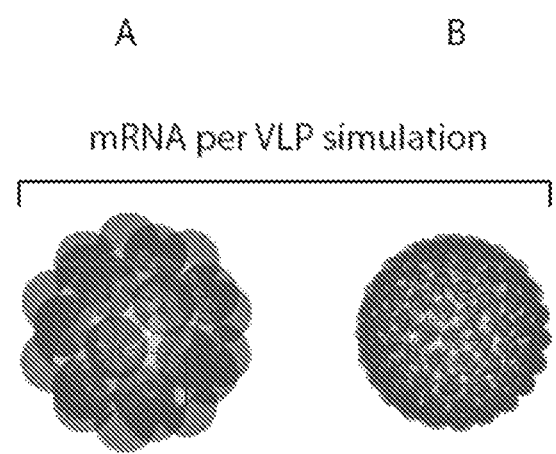
FIG. 7—is a diagram summarizing simulation of export compartment size and the theoretical number of mRNA that could be packaged inside an example export compartment.
Figure 8:
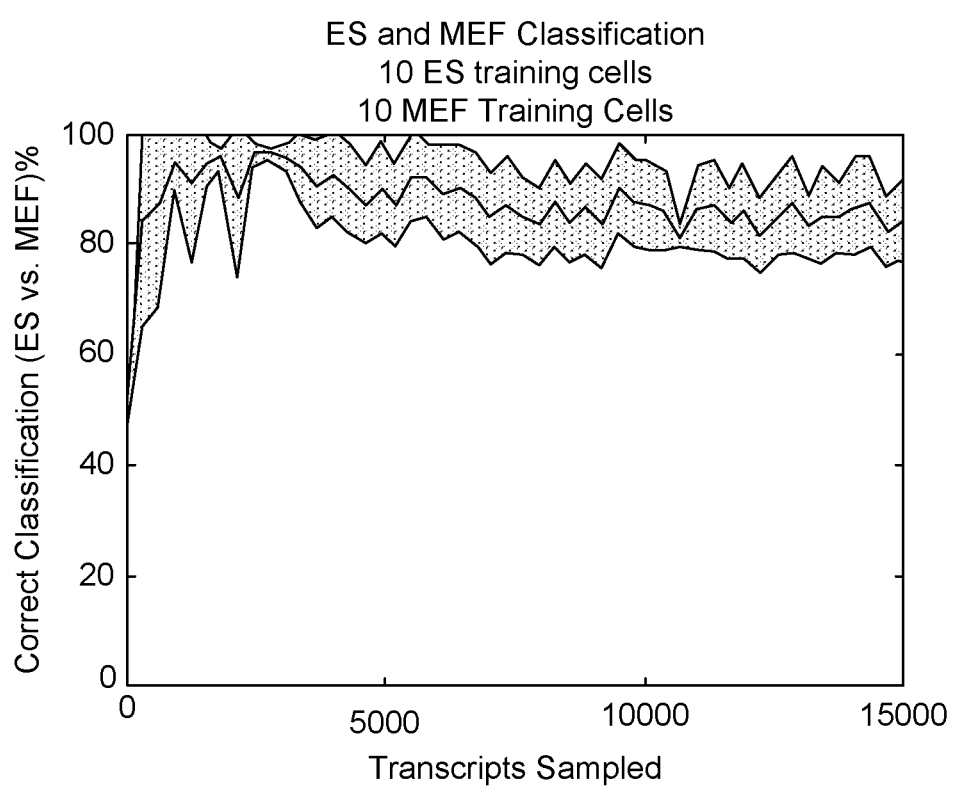
FIG. 8—is a graph showing a simulation based on exclusive reads per cell type that allows for >80% accuracy of prediction with a simple algorithm that uses inner-products and training on 10 cells per cell type.
Figure 9:
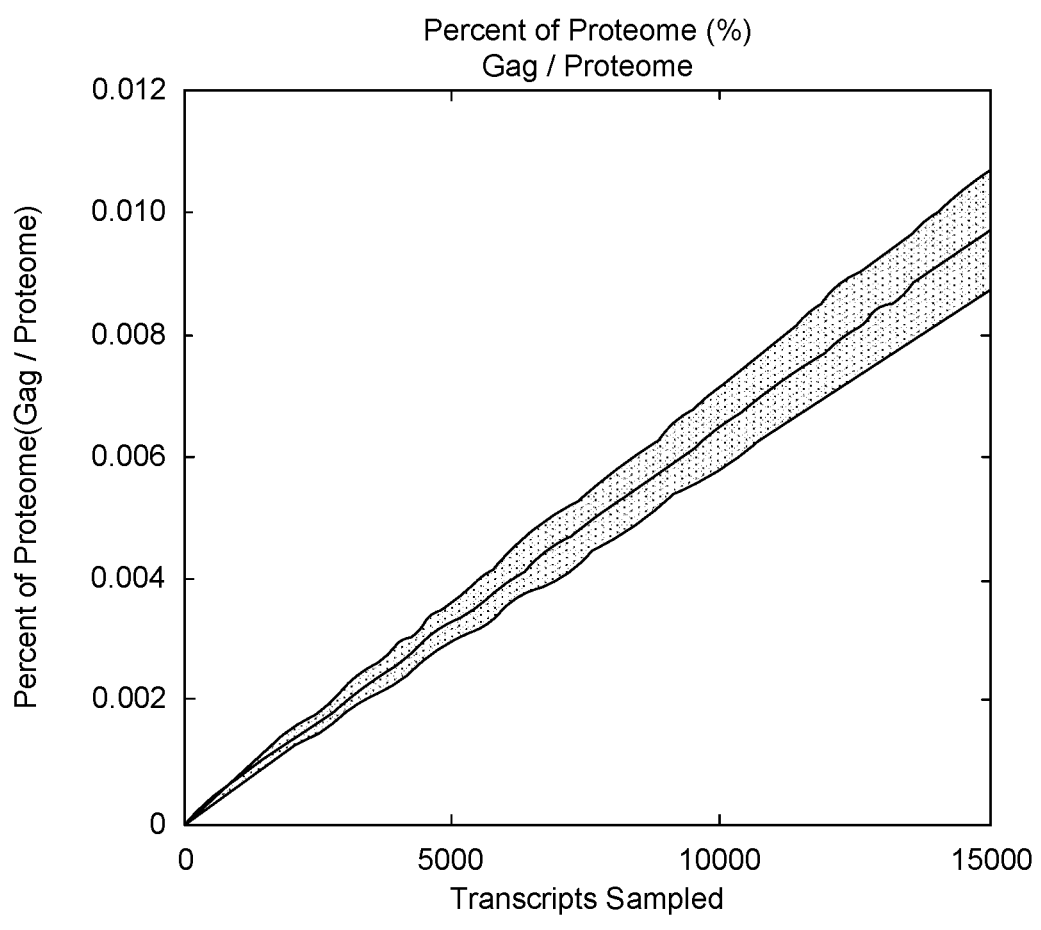
FIG. 9—is a graph showing the percent of the proteome that is composed of Gag proteins per number of transcripts sampled.

In certain example embodiments, all of the constructs disclosed herein may further include an inducible promoter to control expression of the construct elements. Inducible promoters may include any suitable inducible promoter system. As recognized by one of ordinary skill in the art, the suitability of a particular inducible promoter system is dictated by the cellular system in which the constructs will be used. Accordingly, the biotic or abiotic factors that induce the activity of such promoters must be compatible with the cellular system in which the constructs of the present invention will be used. For example, a biotic or abiotic factor that negatively impacts cell viability or significantly alters gene expression of the cell in the context of the biological condition being studied would not be a suitable inducible promoter system. The inducible promoter may be a suitable chemically-regulated promoter or suitable physically-regulated promoter. The chemically-regulated promoter may be a suitable alcohol-regulated promoter, tetracycline-regulated promoter, steroid-regulated promoter, or a metal-regulated promoter. The physically-regulated promoters may be a temperature-regulated promoter or a light-regulated promoter. In certain example embodiments, the inducible promoter is a tetracycline-regulated promoter such as pTet-On, pTet-Off, or pTRE-Tight. In certain example embodiments the promoter is a dox-inducible promoter. In certain other example embodiments, the promoter is a cell-specific or tissue-specific promoter. In certain example embodiments, the construct may comprise both a cell-specific or tissue specific promoter and a second promoter such as dox. See FIG. 5.

In certain example embodiments, all of the constructs disclosed herein may further comprise a steric linker sequence. The encoded steric linker sequence may be a random peptide sequence of a particular size. The size of the steric linker sequence may control the rate of export, the size of the export compartment or both. For example, a larger linker sequence appended to an export compartment protein may slow the rate at which the export compartment proteins can self-assemble by creating steric hindrance that slows the rate of assembly. Likewise, a larger linker sequence that must be incorporated into the export compartment may increase the size of the export compartment formed. In certain example embodiments, the steric linker is approximately 2 to approximately 12 amino acids in size. In certain example embodiments, the linker sequence is located on the N-terminus of the secretion-inducing protein. In certain other example embodiments, the linker sequence is located on the C-terminus of the secretion-inducing protein.

In certain example embodiments, the constructs disclosed herein may further encode an affinity tag. An affinity tag may include, but is not limited to, Flag, CBP, GST, HA, HBH, MBP, Myc, polyHis, S-tag, SUMO, TAP, TRX, and V5. Affinity tags may also include engineered transmembrane domains in order to increase the likelihood of surface presentation. The affinity tags may be then used to purify, for example VLPs, formed by the fusion protein using standard affinity purification techniques. See FIG. 6. The affinity tag may be encoded by the construct such that the affinity tag is located on a N-terminus of the secretion-inducing protein.

Figure 3:
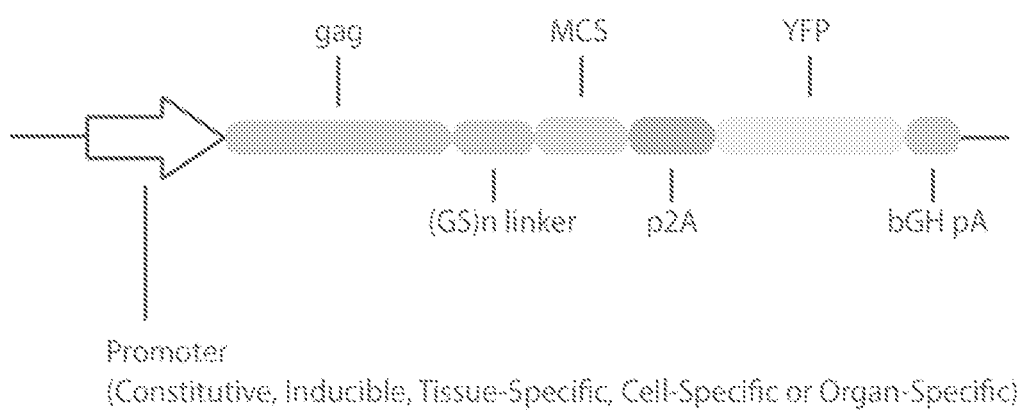
FIG. 3—is a diagram of a construct in accordance with certain example embodiments. The diagram shows a possible DNA construct for making Gag fusion proteins. The glycine-serine (GS) linker (SEQ ID NO: 7) functions as a flexible amino acid linker between the gag protein and the cloned protein of interest. The RNA capture domain of interest is ligated into the construct in the multiple cloning site (MCS) via standard restriction cloning techniques. The p2A linker (SEQ ID NO: 5) serves as a self-cleaving linker, allowing yellow fluorescent protein (YFP) (SEQ ID NO: 6) to be translated from the same transcript without fusion. The DNA construct includes a bGH pA terminator (SEQ ID NO: 8). The construct may include a spacer between elements (SEQ ID NO: 9).

In certain example embodiments, the constructs may further encode an antibiotic resistance gene to facilitate chemical selection of cells or cell populations to which the RNA constructs described herein have been delivered and expressed. In certain example embodiments, the constructs disclosed herein may further encode a detectable self-reporting molecule. In certain example embodiments, the construct may further encode a cleavable linker between the detectable self-reporting molecule and the fusion protein of interest. See FIG. 3. In certain example embodiments, the cleavable linker may be a self-cleaving linker such as P2A. In certain example embodiments, the detectable self-reporting molecule is a fluorescently detectable self-reporting molecule such as RFP, YFP, or GFP. Detection of the self-reporting molecule in a cell or cell population may be used to determine successful delivery and expression of the constructs disclosed herein.

In certain example embodiments, the construct RNA sequences may further encode a nuclear export protein the enables nuclear export of Pol III driven transcript without perturbing cellular localization of other endogenous RNA transcripts. In certain other example embodiments, the barcode sequence may be incorporated into the 5' or 3' UTR of a Pol II driven transcript (e.g. GFP), which is naturally exported to the cytoplasm.

Vectors

In another aspect, the embodiments disclosed herein are directed to vectors for delivering the constructs disclosed herein to cells. In certain example embodiments the vector is a viral vector. Suitable viral vectors include, but are not limited to, retroviruses, lentiviruses, adenoviruses and AAV. In certain other example embodiments, the vector is a non-viral vector. Suitable non-viral vectors include, but are not limited to, cyclodextrin, liposomes, nanoparticles, calcium chloride, dendrimers, and polymers including but not limited to DEAE-dextran and polyethylenimine. Further non-viral delivery methods include electroporation, cell squeezing, sonoporation, optical transfection, protoplast fusion, impalefection, hydrodynamic delivery and magnetofection. For non-viral vectors, delivery to a microbe may be facilitated by standard transfection technologies such as electric pulsing, electroporation, osmotic shock, and polymeric-based delivery systems.

Methods of Live Cell Sampling

The constructs and vectors disclosed herein can be used in methods for continuous live cell sampling enabling the ability to monitor molecular profile changes over time. In certain example embodiments, the exported cellular contents may be barcoded with a cell-specific barcode allowing multiple samples to be processed in bulk while retaining the ability to identify the cell or cell population of origin.

In one example embodiment, a method of single-cell gene expression profiling comprises delivering a nucleic acid construct encoding a fusion protein and a construct RNA sequence to a cell or population of cells. For embodiments utilizing viral vectors, the cell or cells are transduced with the constructs at a low multiplicity of infection. In certain example embodiments, the cells may be subsequently subjected to chemical selection to ensure that all cells have a stable single-copy of the constructs. For example, the constructs may encode an antibiotic resistance gene and chemical selection is carried out by exposure of the cell or cells to a corresponding antibiotic. Alternatively, for those embodiments employing a detectable self-reporting molecule, such as GFP, the self-reporting molecule may be used to assess successful. Cells expressing the self-reporting molecule may then be selected using known methods in the art, such as flow cytometry.

The fusion protein comprises a secretion-inducing domain and a construct RNA capture domain. The construct RNA sequence comprises a retrieval element and a cellular RNA capture element. The construct RNA sequence may further comprise a barcode. The barcode comprises a nucleic acid sequence unique to the nucleic acid construct delivered to the cell. The cellular RNA capture element binds cellular RNA by hybridizing to the cellular RNA. In certain example embodiments the construct RNA sequence hybridizes to mRNA via a poly-U sequence or sequence comprising a repeating (UUG)n motif. In certain example embodiments, the secretion-inducing domain is an export compartment protein described herein that self-assembles to form an export compartment. In the process of self-assembling to form the export compartment the construct RNA capture domain binds the retrieval element on the construct RNA sequence resulting in the packaging of both the construct RNA sequence and any cellular RNA hybridized to the construct RNA sequence via the construct RNA sequence's cellular retrieval element. The export compartment is then exported from the cell. For example, the export compartment may be released into the cell culture media. The media may then be collected and the sample isolated. For example, the export compartments may be isolated from the cell culture media by ultracentrifugation, or other methods that separate components based on size or density. In certain example embodiments, the fusion protein further comprises an affinity tag as described above, which may be used to isolate and enrich for the export compartments using standard affinity purification techniques known in the art.

Figure 2:
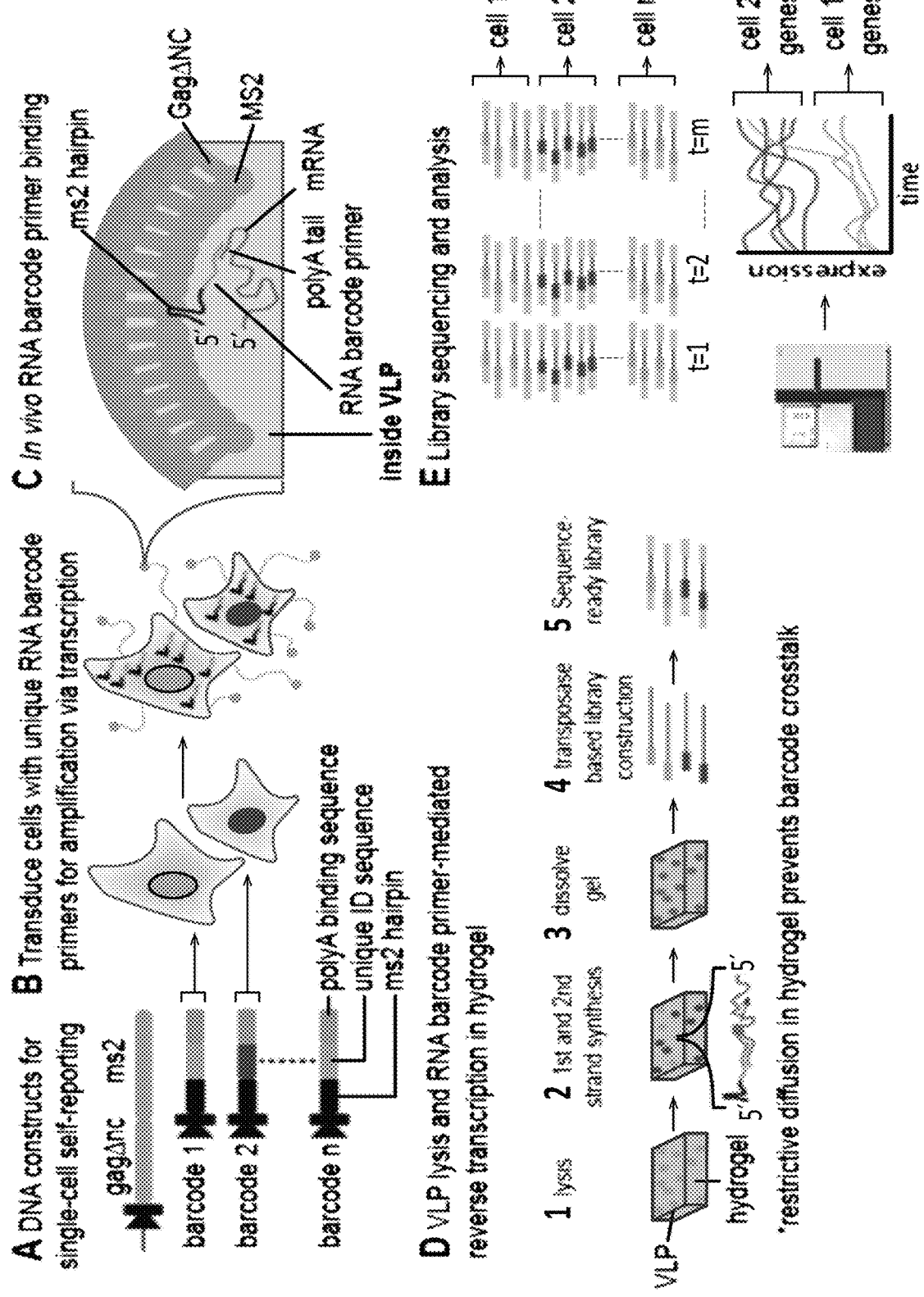
FIG. 2—is a diagram depicting a barcoded self-reporting strategy in accordance with certain example embodiments.

The isolated export compartments may then be lysed and the exported cellular RNAs retrieved. In certain example embodiments, the isolated VLPs are placed into a hydrogel. The VLPs are then lysed and first and second strand synthesis as described above is conducted within the hydrogel. The hydrogel is then dissolved and sequencing library preparation conducted as described above. The restrictive diffusion provided by the hydrogel may be used to prevent potential barcode cross-talk during the RT reaction steps. See FIG. 2.

After RNA collection, RNA sequences may be permanently linked to the cellular barcodes by utilizing the barcoded construct RNA sequence as a primer for reverse transcription thereby incorporating the barcode in the resulting RNA-DNA duplex. Likewise, in certain example embodiments, the poly-A tail of cellular mRNA may be used to reverse transcribe the barcode portion of the construct RNA sequence. In certain example embodiments a primer designed to bind to the barcode sequence, or a portion thereof, may be used to initiate reverse transcription. See FIG. 1. Various example embodiments for incorporation of the barcode sequence into DNA amplicons suitable for sequencing analysis are discussed below.

Figure 11:
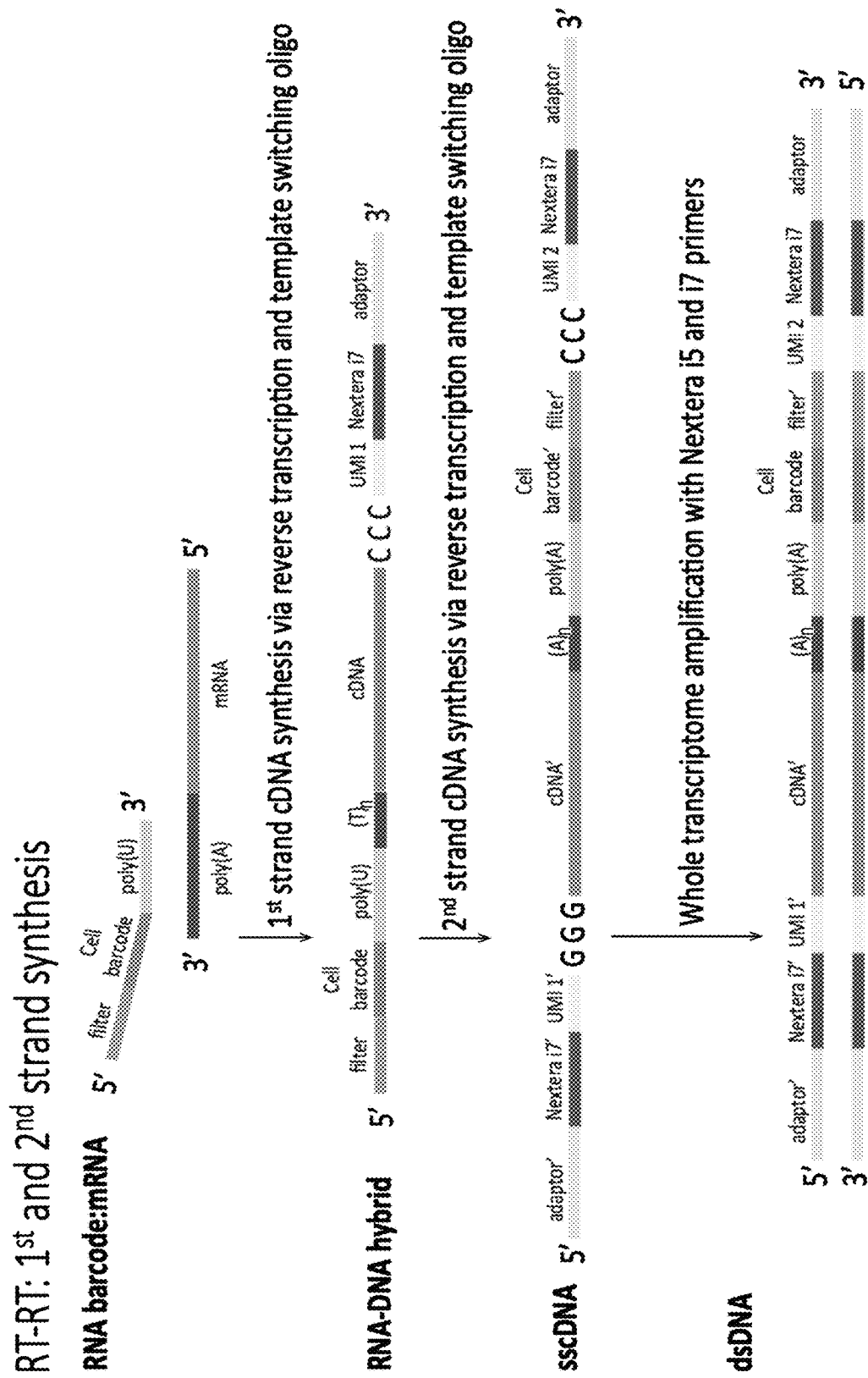
FIG. 11—is a schematic showing one example embodiment for incorporation of barcodes of dsDNA amplicons derived from cellular mRNA isolated from export compartments.

Discussion of the following example embodiment is made with reference to FIG. 11. The RNA construct sequence comprises at least, in a 5' to 3' direction, a retrieval element, a filter, a barcode, and a poly(U) or $(UUG)_n$ motif for binding to poly-A tails cellular mRNAs. The RNA construct sequence is used to prime first strand cDNA synthesis via reverse transcription of the mRNA template. Template switching may be used to incorporate sequences from a template switching oligonucleotide. For example, a MLV reverse transcriptase—or similar reverse transcriptase—may be used to add non-template nucleotides to the first-strand cDNA when it reaches the 5' end of the mRNA. Template switching oligonucleotides designed to bind to these non-template nucleotides may then be used to facilitate template switching and incorporation of sequences complementary to the template switching oligonucleotide. In certain example embodiments, the template switching oligonucleotide may be used to introduce, in a 5' to 3' direction, a unique molecular identifier (UMI), a first sequencing primer binding site, and an adapter sequence. A UMI is a short nucleotide sequence (e.g. six to eight bp) that uniquely identifies each template switching oligonucleotide. Next a second cDNA strand is synthesized via reverse transcription and use of a second template switching oligonucleotide resulting in the single stranded cDNA (sscDNA). Double-stranded DNA amplicons suitable for sequencing analysis are then generated by amplification of the sscDNA using the sequencing primer binding sequences introduced into the sscDNA.

Figure 12:
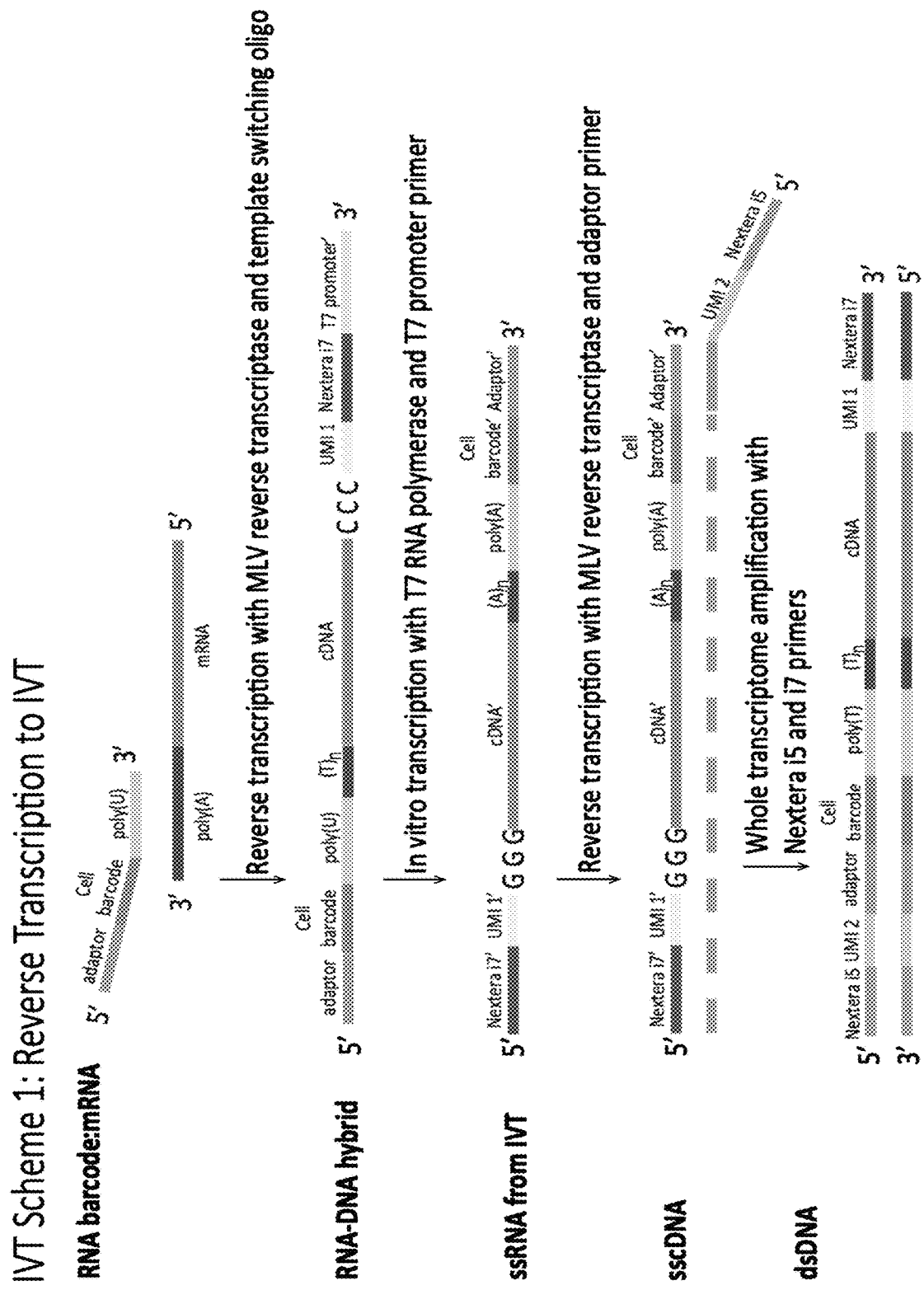
FIG. 12—is a schematic showing one example embodiment for incorporation of barcodes into dsDNA amplicons derived from cellular mRNA isolated from export compartments.

Discussion of the following example embodiment is made with reference to FIG. 12. The construct RNA sequence may comprise, in a 5' to 3' direction, an adapter sequence a barcode and a poly(U) or $(UUG)_n$ motif. Lysis of export compartments may be completed in hydrogels as described above. As in the previous embodiment, the construct RNA sequence is used to first prime a reverse transcription reaction that results in addition of a UMI sequence, sequencing primer binding sequence and the complement of a RNA polymerase promoter (such as a complement of a T7 promoter) and the RNA-DNA hybrid show in FIG. 12. A single stranded RNA copy is then generated from the RNA-DNA hybrid by in vitro transcription with a RNA polymerase and RNA polymerase promoter. A single stranded cNDA (sscDNA) is then generated by reverse transcription primed by an adapter primer that binds its complementary sequence incorporated into the ssRNA. The adapter primer may further comprise a second UMI and a second sequencing primer binding sequence. Double-stranded DNA amplicons suitable for sequencing analysis are then generated by amplification of the dscDNA product using a first and second sequencing primer complementary to the first and second sequencing primer binding sequences.

Figure 13:
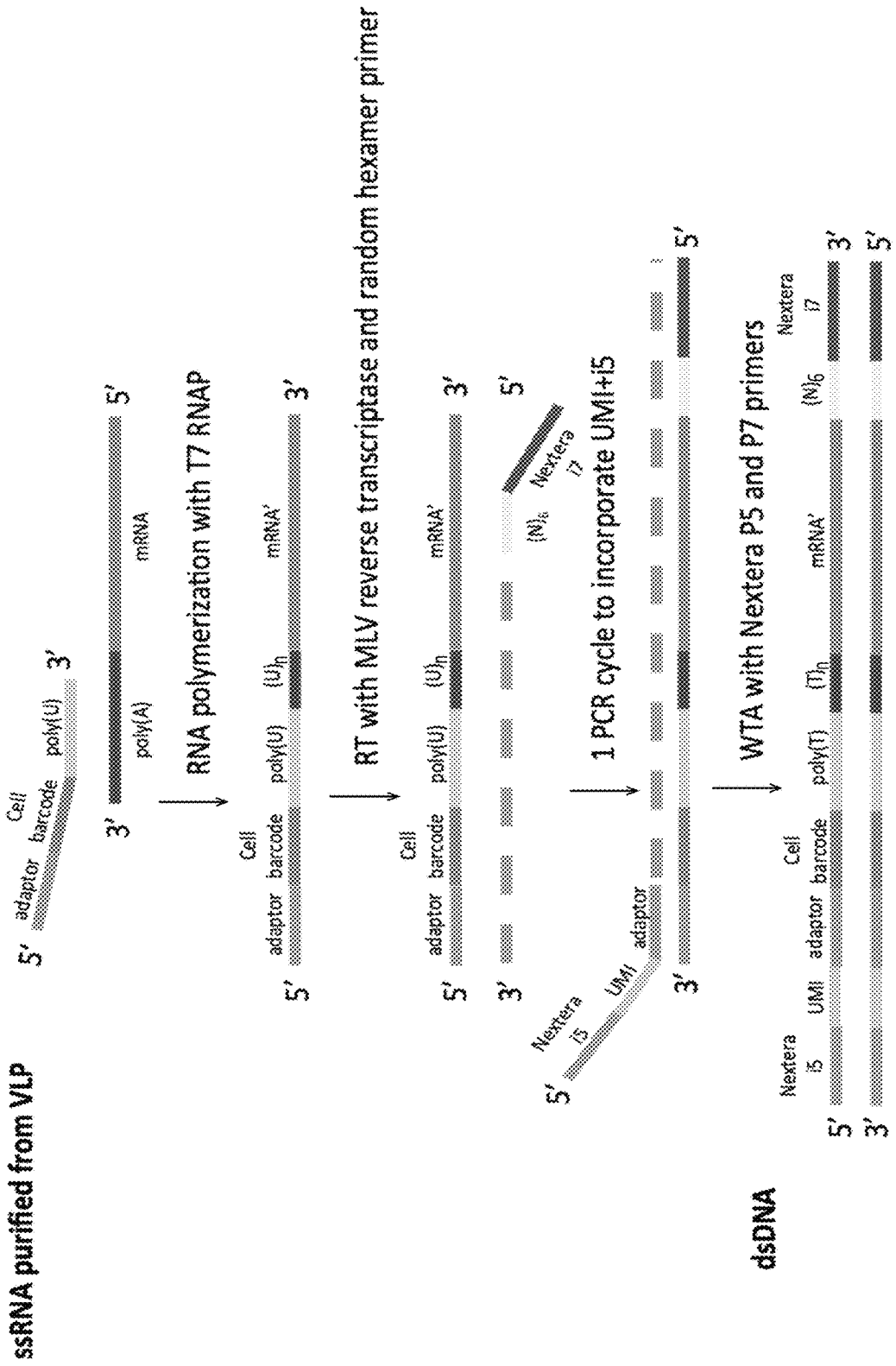
FIG. 13—is a schematic showing one example embodiment for incorporation of barcodes into dsDNA amplicons derived from cellular mRNA isolated from export compartments.

Discussion of the following example embodiment is made with reference to FIG. 13. The same construct RNA sequence architecture described above may be used to prime RNA polymerization using T7 RNAP, or similar RNA polymerase, to generate a RNA complement of the cellular mRNA. A reverse transcription reaction is then conducted using a reverse transcription primer, the reverse transcription primer comprising, in a 5' to 3' direction, a sequencing primer binding sequence and a random hexamer motif. The resulting RNA comprises the original mRNA sequence with the random hexamer and first sequencing primer binding site sequence appended to the 5' end and the cell barcode and adapter sequence appended to the 3' end. A single PCR cycle using as second primer is conducted to generate a DNA: RNA hybrid, the second primer comprising, in a 5' to 3' direction, a second sequencing primer binding site, a UMI, and complementary adapter binding sequence. This reaction incorporates the second sequencing primer binding site and UMI into the DNA:RNA hybrid. The DNA:RNA hybrid is then amplified through whole transcriptome amplification using the first and second sequencing primers. The resulting dsDNA amplicons may then be prepped for sequencing using standard methods known in the art.

Figure 14:
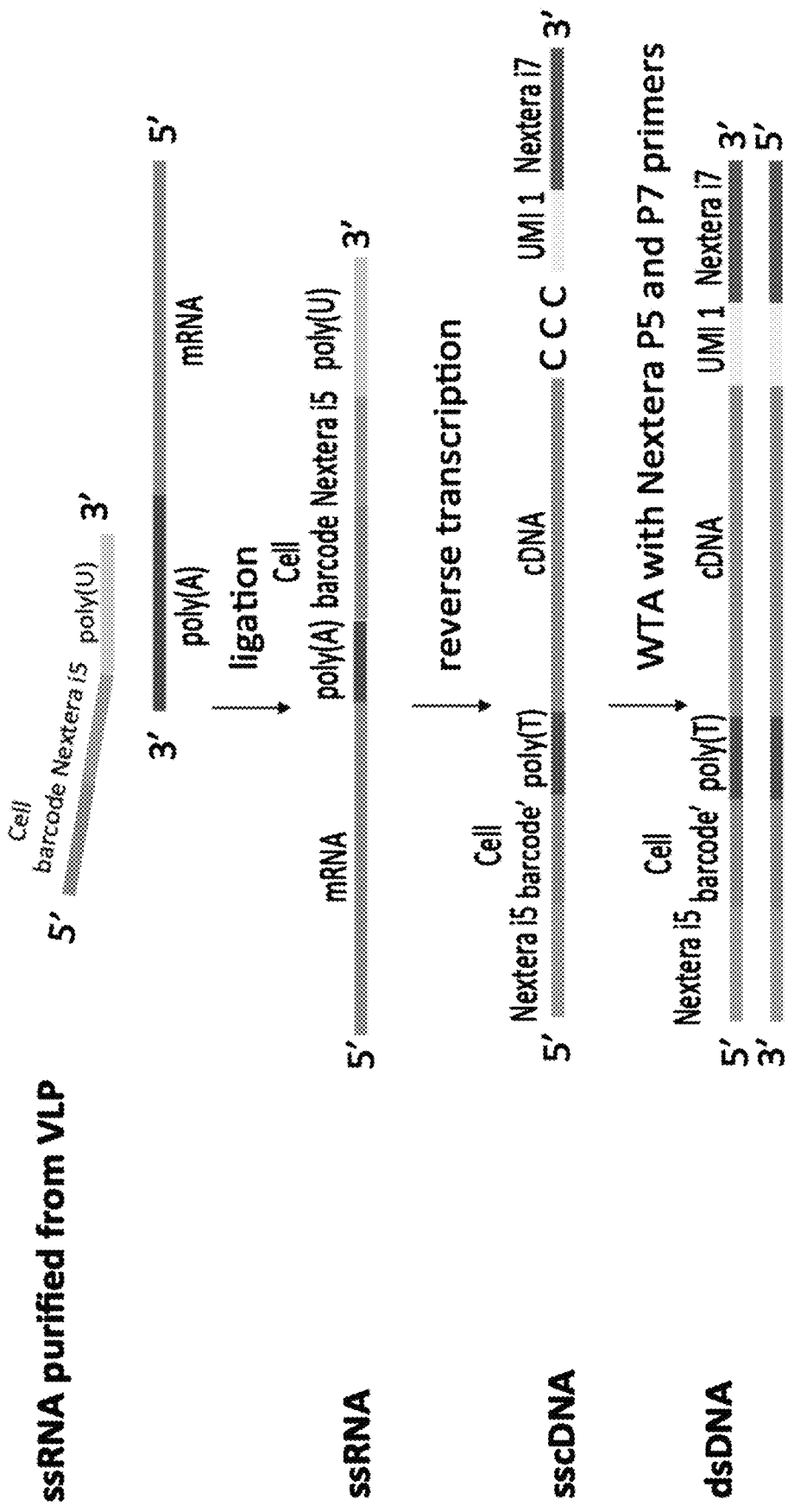
FIG. 14—is a schematic showing one example embodiment for incorporation of barcodes into dsDNA amplicons derived from cellular mRNA isolated from export compartments.
Figure 15:
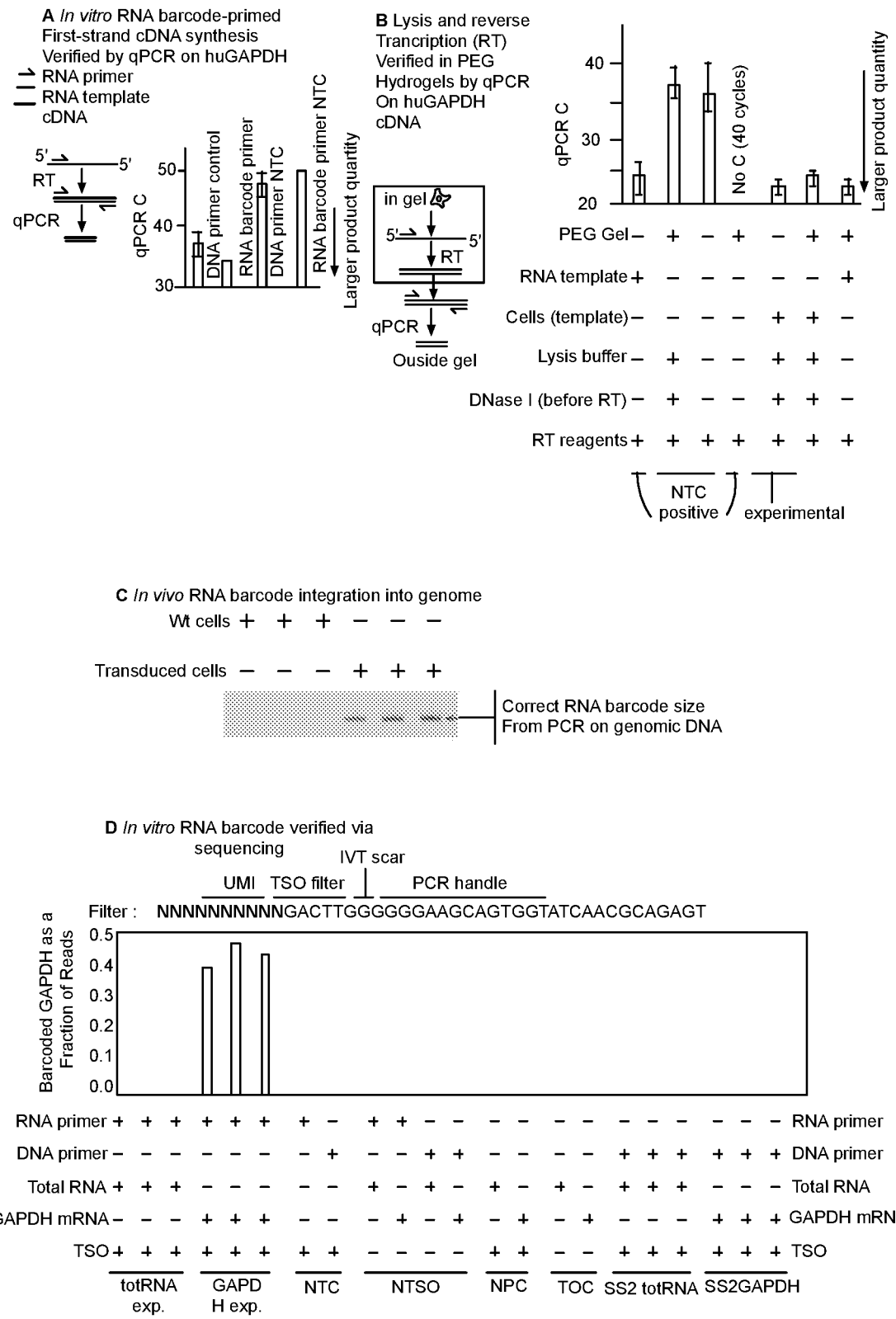
FIG. 15—A) Reverse transcription with RNA primers. B) Reverse transcription in crosstalk-preventing hydrogels with RNA primers. C) Genomic integration of synthetic RNA barcodes in HEK cells by lentiviral transduction. D) Efficient in vitro library construction of RNA barcoded monoclonal RNA template. The filter may include a Smart-seq2 handle (SEQ ID NO: 11).

Discussion of the following alternative example embodiments is made with reference to FIG. 14. The construct RNA sequence may comprise, in a 5' to 3' direction, a barcode a first sequencing primer binding site, a poly(U) or (UUG)$_n$ motif. The construct RNA sequence hybridizes to the poly-A tail of the mRNA via the poly(U) or (UUG)$_n$ motif. The 5' end of the RNA construct sequence is then ligated to the 3' poly-A tail of the mRNA. In certain example embodiments, the mRNA-construct RNA duplex may be further stabilized prior to ligation by cross-liking the poly-A and poly(U) sequences, for example using a psoralen. After ligation cross-linking is reversed. The ligated single stranded mRNA product then comprises, in a 5' to 3' direction, the cellular mRNA sequence, barcode, first sequencing primer binding site, and poly(U). The mRNA is reverse transcribed into cDNA as previously described resulting in barcoded cDNA. A second reverse transcription reaction is then primers using a primer comprising a complementary sequence to the non-template nucleotides added by the first RT reaction, a UMI, and a second sequencing primer binding site. The resulting dsDNA product is then amplified by whole transcriptome amplification using first and second sequencing primers that hybridize to the first and second sequencing primer binding sites. The resulting dsDNA amplicons may then be prepped for sequencing using standard methods known in the art.

Transcripts with the same unique barcode may then be identified as originating from the same cell or cell population. Isolated export compartments may be collected over multiple time points from the same cells or population of cells. As noted above, the constructs may further include an inducible promoter to control at what time points the expression of the export compartment is turned on and off.

In addition, to using sequenced barcode information to identify the origin of particular transcripts, optical detection of the barcodes may also be used to match single-cell gene expression profiles with microscopy. Combination with microscopy allows the tissue context of the assayed cells to be derived as well as key measures of cell morphology and protein levels. For example, optical detection of the barcodes would allow relationships between transcriptional changes involving many genes and optically observable phenomena to be tracked in coordinated time-lapse measurements at the single-cell level. A set of probes may be derived with each probe cable of specifically hybridizing to a given oligonucleotide tag in the barcode. Each probe for a given oligonucleotide sequence may be labeled with a different optically detectable label. In one example embodiment, the optically detectable label is a fluorophore. In another example embodiment, the optically detectable label is a quantum dot. In another example embodiments, the optically detectable label is an object of a particular size, shape, color, or combination thereof. For each position in the barcode, the corresponding set of probes for each oligonucleotide tag at that position is allowed to hybridize to the cells in situ. The process is repeated for each position in the barcode. Therefore, the observed pattern of optically detectable barcodes will be dictated by the order of oligonucleotide sequences in the barcode. Accordingly, the barcode may be determined by the optical readout obtained with sequential hybridization of probes.

In certain example embodiments, a set of fluorescently labeled probes specific to each oligonucleotide tag segment of the barcode may be sequentially hybridized to the cells in situ, for example, using sequential FISH. Each probe is labeled with a different fluorophore. Therefore, the sequence and order of the oligonucleotide tags in the barcode will dictate the order of colors observed using fluorescence microscopy allowing the barcode sequence to be determined optically.

The embodiments are further described in the following examples, which do not limit the scope of the invention described in the claims.

EXAMPLES

Example 1—Continuous Monitoring Constructs

Mammalian cells turn over approximately 14% of the transcriptome per hour on average (Yang E, Genome Research 2003), and simulations (described below) show that mRNA can theoretically be exported in VLPs at 100% of the cell's normal synthesis rate. By sampling at 25% of the turnover rate, 3% of the total transcriptome could be sampled per hour, or 500-15,000 transcript molecules per hour. By fine-tuning the transcriptional and translational dynamics of export compartment production, cellular RNA should be sampled at a specified rate of 0.1% to 3% of the normal synthesis rate. Even with estimated sample preparation methods that are approximately 50% efficient, detection of 250-7500 collected transcript molecules per cell per hour can be achieved. This 'integration time' can be varied to resolve the necessary timescales associated a particular question. A tunable trade-off exists between temporal resolution and the degree of perturbation to the cell.

Packing of 28-150 transcripts per VLP inner surface is estimated. This estimate is derived from a range in VLP radius of 80-130 nm and an mRNA radius of gyration of 16.8-20.8 nm (mRNA radius of gyration from Gopal A, RNA 2012). With these numbers in mind, it is possible to calculate that the burden of VLP production necessary to collect 15,000 transcript molecules per hour corresponds to as little as 0.01% of the cell's total protein (total protein per cell count from Siwiak M, PLoS ONE 2013).

To export mRNA in a minimally-biased manner for genome-wide expression profiling, a Gag-PABP fusion was constructed and export tested from HEK293 cells. The construct is safe and replication-deficient, as it contains neither reverse transcriptase nor integrase. See FIG. 3. Poly(A)-binding protein (PABP), which binds to the poly(A) tail of mRNA, can be used as an mRNA binding domain for synthetic mRNA export machinery. The PABP domain will recruit mature transcripts from the cytoplasm, while the Gag domain will allow for export of captured mRNA through membrane budding and VLP formation. The overall rate of export can be optimized for the desired sampling frequency and cell type by controlling the Gag-PABP fusion expression level.

Figure 4:
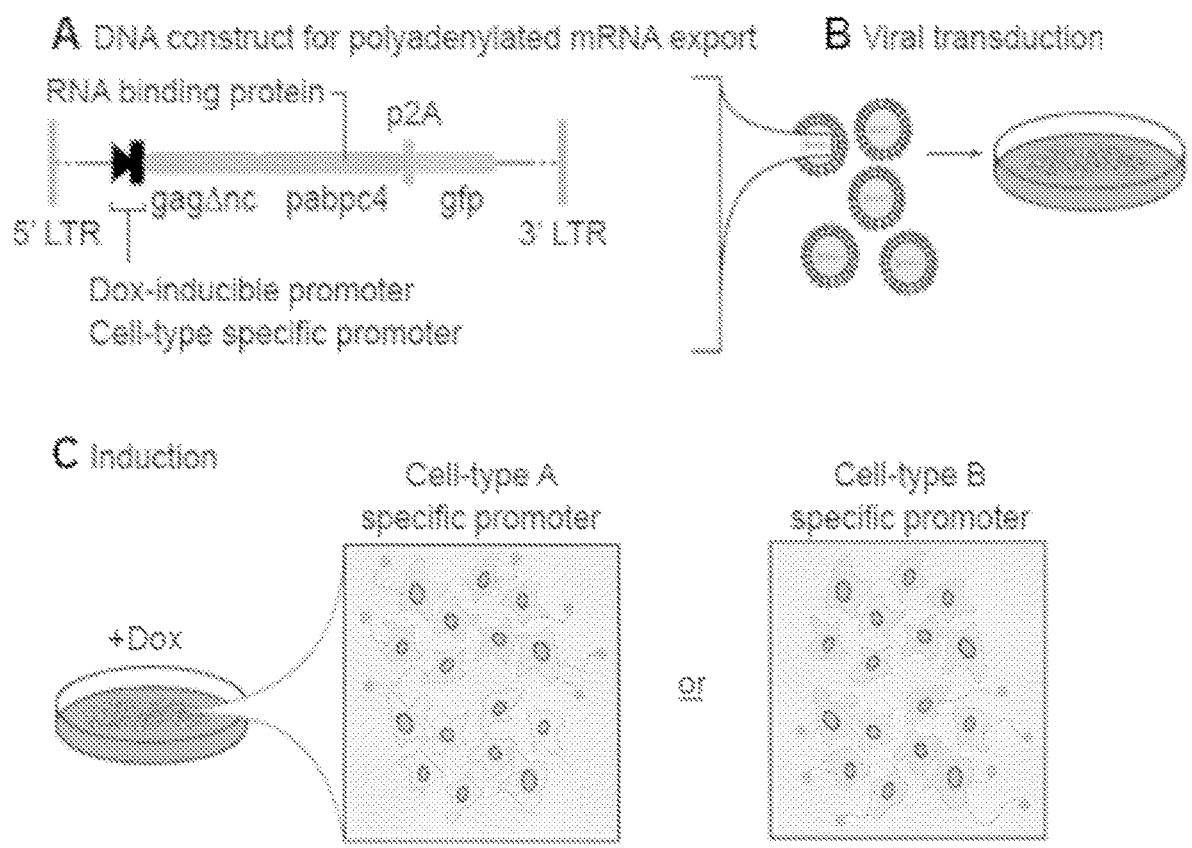
FIG. 4—is a schematic of single-cell expression analysis using an example inducible construct further encoding a construct self-reporting molecule that may be used to indicate successful delivery to target cells, in accordance with certain example embodiments.

A rate of VLP export of mRNA can be determined by carrying out highly controlled VLP collection experiments with an inducible Gag-PABP fusion from a known number of cells. RNA from the VLPs can then be extracted and used to prepare RNA-Seq libraries (FIG. 4) with unique molecular identifiers and a spike-in control (ERCC from Life Technologies). By comparing the RNA-seq of bulk cell lysate of self-reporting cells to the lysate of normal cells, the transcriptional defect caused by the VLP export system can be detected. Similar analysis of the extracted VLPs compared to bulk controls can be used to estimate mRNA export per cell per unit time and any sampling biases (eg against large transcripts). These tests are carried out over a range of different promoter strengths to find the optimal expression rate, for all cells of interest.

Next, GFP+ self-reporting HEK293 cells are plated in such a way that there is 1 cell per well of a 384 well plate on average. To remain certain that GFP+ cells are self-reporting, GFP and Gag-PABP are delivered in the same vector. This experiment allows the plate to be imaged to determine the number of GFP+ self-reporting cells, the media retrieved to collect VLPs. After collection, VLPs are purified by standard virus purification protocols. VLP lysis is carried out using standard lysis techniques, and Illumina-ready DNA libraries are constructed using Smart-seq2 (Picelli S, Nature Protocols 2014). By indexing the media from each well separately through the Smart-seq2 protocol, the sequencing reads can be traced to the original wells to determine the accuracy of VLPs as reporter systems. This can enable GFP expression as a function of time to be observed, and a correlation between GFP reads and cell fluorescence to be determined. The individual cells are collected at the final time point and collected and prepared for RNA-Seq in the same plate.

Example 2—Barcoded Constructs

Contents from single-cells are barcoded by expressing a unique randomized RNA sequence with a MS2 hairpin. By hybridizing these barcodes to export mRNA, a barcode-mRNA hybrid can be created with reverse transcription after collecting VLPs. To test single-cell mRNA barcoding and export strategy, a modified version of the collection methods described above are used. Gag is fused to a MS2 coat protein, which binds the MS2 RNA hairpin with nanomolar binding affinity. By transducing or transfecting cells with a MS2 hairpin containing a cell-specific unique random barcode and a 3' polyU sequence, it is possible to capture and export mRNA in an unbiased fashion, with each transcript stably hybridized to the barcoded MS2 capture probe by the poly(A):poly(U) interaction. After VLP collection transcript sequences are permanently linked to the cellular barcodes by utilizing the barcoded MS2 transcript as a primer for reverse transcription (RT). Such RNA-primed RT has been previously demonstrated and even shown to result in higher fidelity than DNA-primed RT (Oude E, JBS 1999). Further, M-MULV RT enzyme has been shown to use both RNA and ssDNA as a template (Verma, B B A 1977), allowing the RNA-DNA hybrids to be converted completely to DNA after a second strand synthesis step with a DNA primer. See FIG. 1.

The molecular biology steps are tested using in vitro transcribed barcoded MS2 hairpin RNA and purified total RNA. The $(UUG)_n$ motif in the capture sequence is used to prevent early transcriptional termination from pol III promoters, as a stretch of 4 or more uracil bases leads to a 90% transcription termination efficiency (Orioli A, NAR 2011). Reverse transcription with a (TTG) DNA primer has been verified as efficient as its poly(T) analogue. The in vitro experiment are read out by RT-qPCR of Gapdh-MS2 fusion cDNA. Next, the same assessment is performed using supernatant from transduced HEK293 cell lysates to demonstrate and optimize endogenous transcript capture by the MS2 barcode transcript. Transcript capture and RNA-primed RT from secreted VLPs from bulk HEK293 cultures are tested and complements the RT-qPCR readout with RNA-Seq of the fusion products (including spike-in controls) to determine export rates and bias compared with total lysate from the same cell population.

Example 3

Single-cell trans-differentiation trajectories can be monitored by delivering unique RNA barcodes along with the Gag export machinery described here. To do this we can transduce HT1080 fibroblasts with unique RNA barcodes as well as Gag export machinery. Further, can same HT1080 fibroblasts can be transduced with a MyoD construct to initiate the trans-differentiation to a myoblast lineage. Bulk population controls and single-cell controls (without export machinery) along the time course can be used to validate the observed cell-states along each trajectory. By collecting supernatant, and building single-cell barcoded libraries with methods described here, temporal RNA information can be tied back to each individual cell of origin. After carrying out dimensionality reduction and other machine learning techniques on the RNA-seq data, it is possible to map single-cell trans-differentiation trajectories.

Example 4—Nuclear Export of Barcoded Constructions

Figure 16:
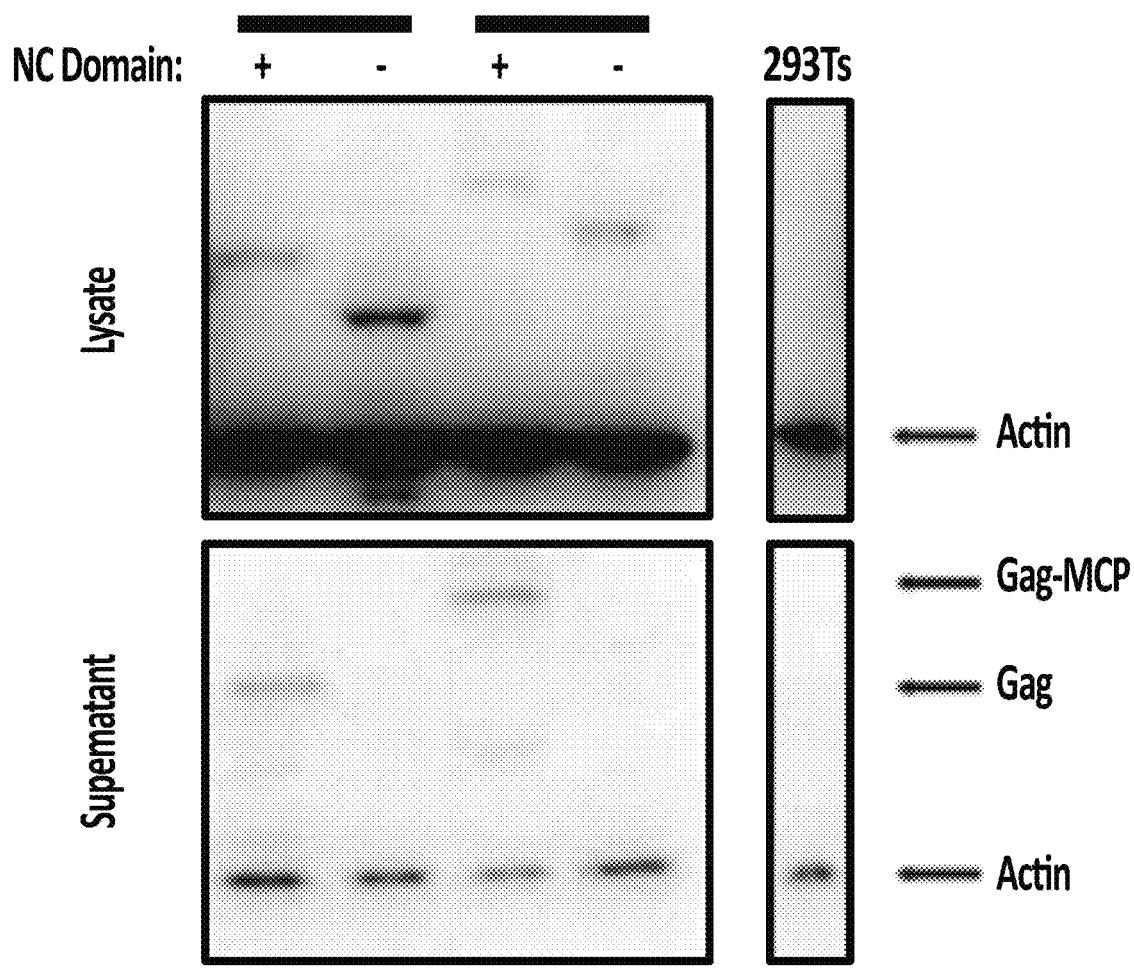
FIG. 16—A) Gag-MCP (Gag-MS2) forms VLPs as demonstrated by an anti-Gag western supernatant. B) Pol III driven RNA barcodes transcripts contain a 5' rev response element and are co-expressed with Rev viral proteins for nuclear export. RNA barcode transcripts are engineered with MS2 hairpins for binding to the MS2 coat protein (MCP) domain within gag-MCP fusion proteins. Barcodes are expressed within wild-type gag expressing cells (to serve as a measure of background export) and within gag-MCP expressing cells for directed export within gag-MCP VLPs. Barcodes either contain a 3' poly(U) tail for hybridizing to polyadenylated RNAs or a scrambled 3' tail as a hybridization control. C) Gag-MCP VLPs successfully package and export endogenous mRNA, as measured by GAPDH RT-qPCR.
Figure 16:
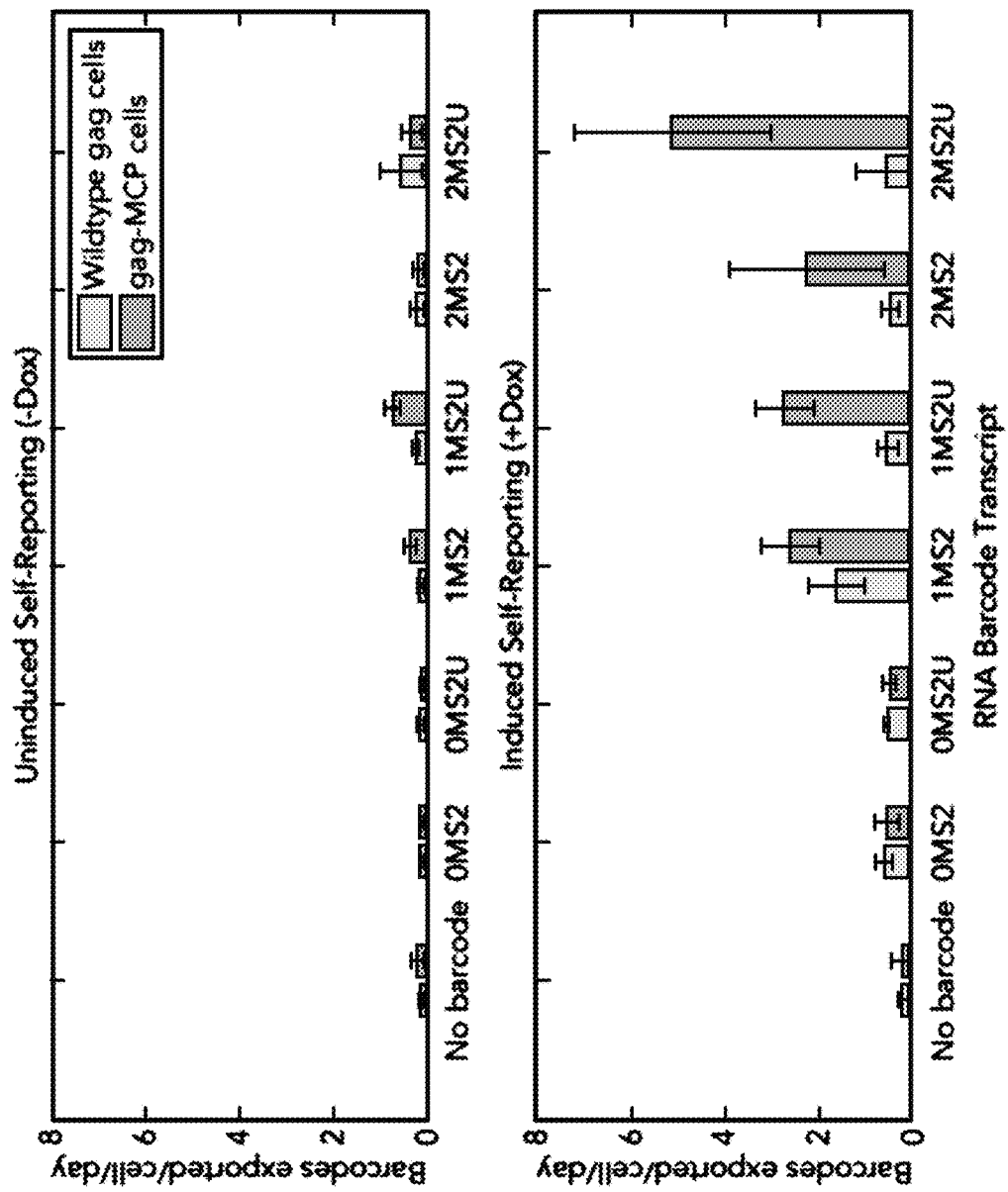
Figure 16:
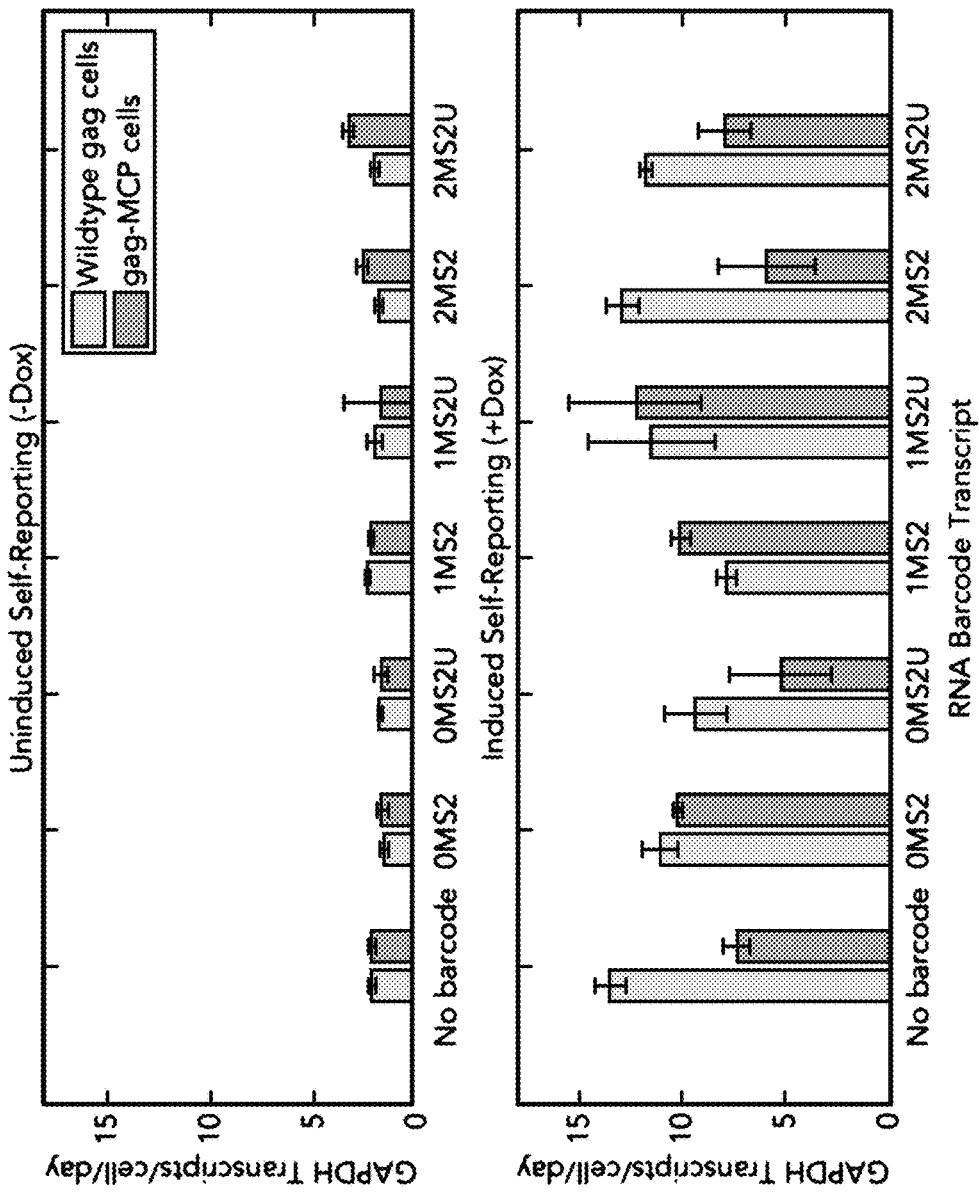

Self-reporting enables a non-destructive assessment of a cell's transcriptional state by packaging representative fractions of a cell's transcriptome into virus-like particles (VLPs), which are subsequently exported from the cell into the culture environment. In population culture of self-reporting cells, genetic encodings may be needed to map the RNA exported with VLPs to the cell of origin. Thus, a synthetic transgene was engineered to encode cell state information (e.g. cell type, cell lineage, genetic perturbation, etc.) into an RNA transcript—termed an RNA barcode—for packaging and export with VLPs. RNA barcodes are designed to be U6 promoter driven, small RNA transcripts that can be stably expressed in cells via viral delivery. Gag viral proteins bind and complex with cytoplasmically expressed RNAs. Thus, nuclear export of the RNA barcode is achieved by including the Rev Response Element (RRE) in the 5' of the transcript and independently co-expressing the HIV-1 Rev viral protein from the same lentiviral vector. Upon expression, Rev protein binds its cognate RRE motif within the RNA barcode transcripts to promote Ran-GTP mediated nuclear export. The RNA barcode transcripts also contain MS2 hairpins that can bind the MS2 coat protein (MCP) domain within gag-MCP fusion proteins to specifically enrich the packaging of RNA barcode transcripts within gag-MCP VLPs. See FIG. 16.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A nucleic acid construct comprising a nucleic acid sequence encoding a fusion protein and a construct RNA sequence, the fusion protein comprising a viral export compartment protein and a construct RNA sequence capture domain, the construct RNA sequence comprising a retrieval element capable of binding the RNA sequence capture domain and a cellular polyadenylated RNA capture element, wherein expression of the fusion protein in one or more cells induces export of cellular polyadenylated RNAs bound to the cellular polyadenylated RNA capture element.

2. The nucleic acid construct of claim 1, wherein the viral export compartment protein self-assembles upon expression to form an export compartment.

3. The nucleic acid construct of claim 1, further encoding one or more of:
   an inducible promoter to control expression of the nucleic acid sequence encoding the fusion protein;
   an affinity tag such that the affinity tag is displayed with the viral export compartment protein when expressed;
   a linker sequence of a particular size, the size of the linker sequence controlling the rate of formation of an export compartment, a size of the export compartment, or both;
   a detectable self-reporting molecule to detect successful delivery and expression of the nucleic acid constructs;
   a barcode sequence in the construct RNA sequence; and
   a nuclear export sequence in the construct RNA sequence to facilitate export of construct RNA sequences to the cytoplasm.

4. The nucleic acid construct of claim 3, wherein the barcode sequence is a randomized nucleic acid sequence of approximately 10 to approximately 40 nucleotides.

5. A system comprising the nucleic acid construct of claim 3 and a nucleic acid construct expressing a nuclear export protein that facilitates nuclear export of the construct RNA sequence via the nuclear export sequence of the construct RNA sequence.

6. The system of claim 5, wherein the nuclear export sequence encodes a viral nuclear export protein, and wherein the viral export protein is a Rev viral protein.

7. A kit comprising the system of claim 5.

8. The nucleic acid construct of claim 1, wherein the viral export compartment protein is a viral capsid protein, and wherein the viral capsid protein is a Gag protein, and wherein the Gag protein is a lentivirus Gag protein.

9. The nucleic acid construct of claim 1, wherein the nucleic acid sequence encoding the viral export compartment protein is SEQ ID NO: 1.

10. The nucleic acid construct of claim 1, wherein the construct RNA sequence capture domain is MS2 coat protein or dCas9.

11. The nucleic acid construct of claim 1, wherein the nucleic acid sequence encoding the retrieval element of the construct RNA sequence is SEQ ID NO: 10.

12. The nucleic acid construct of claim 1, wherein the retrieval element on the construct RNA sequence is a dCas9 guide RNA sequence or a MS2 hairpin sequence.

13. The nucleic acid construct of claim 1, wherein the cellular RNA capture element of the construct RNA sequence is a poly-U sequence, and optionally wherein the poly-U sequence is approximately 15 to approximately 50 nucleotides long.

14. The nucleic acid construct of claim 1, wherein the cellular RNA capture element comprises a $(UUG)_n$ motif, and wherein n is approximately 1 to approximately 20.

15. The nucleic acid construct of claim 1, wherein the viral export compartment protein self-assembles to form an export compartment approximately 10 nm to approximately 500 nm in diameter.

16. A vector comprising the nucleic acid construct of claim 1.

17. The vector of claim 16, wherein the vector is a non-viral or viral vector.

18. A kit comprising the vector of claim 16.

19. A kit comprising the nucleic acid construct of claim 1.

20. A method for continuous monitoring of live cells comprising:
delivering into one or more cells a nucleic acid construct encoding a fusion protein and a construct RNA sequence, the fusion protein comprising a viral export compartment protein and a construct RNA sequence capture domain, and the construct RNA sequence comprising a retrieval element capable of binding the RNA sequence capture domain, a barcode, and a cellular polyadenylated RNA capture element;
expressing the nucleic acid construct in the one or more cells;
capturing cellular polyadenylated RNA expressed in the one or more cells by binding the cellular polyadenylated RNA via the cellular polyadenylated RNA capture element of the construct RNA sequence;
exporting the cellular polyadenylated RNA from the cell by binding of the fusion protein construct RNA capture element to the retrieval element of the construct RNA such that the cellular polyadenylated RNA is exported from the cell in association with the viral export compartment protein, wherein the viral export compartment protein self-assembles to form an export vesicle; and
isolating the exported vesicles containing captured cellular polyadenylated RNA transcripts at one or more time points.

21. The method of claim 20, further comprising:
generating a RNA-DNA duplex by reverse transcribing the captured cellular polyadenylated RNA using the construct RNA sequence as a primer for reverse transcription;
generating a DNA-DNA duplex by converting the construct RNA sequence to a corresponding DNA sequence with a second strand synthesis using a DNA primer such that the barcode sequence is included in the DNA-DNA duplex;
generating a sequencing library from the generated DNA-DNA duplexes;
sequencing the sequencing library to identify the captured cellular polyadenylated RNA wherein the one or more cells from which the cellular polyadenylated RNA was isolated are identified from the sequenced barcode.

22. The method of claim 20, wherein the nucleic acid construct is delivered using a non-viral or a viral vector.

* * * * *

UNITED STATES PATENT AND TRADEMARK OFFICE
CERTIFICATE OF CORRECTION

| | | |
|---|---|---|
| PATENT NO. | : 11,702,661 B2 | Page 1 of 1 |
| APPLICATION NO. | : 16/335512 | |
| DATED | : July 18, 2023 | |
| INVENTOR(S) | : Blainey et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 881 days.

Signed and Sealed this
Thirty-first Day of December, 2024

Derrick Brent
*Acting Director of the United States Patent and Trademark Office*